(12) United States Patent
Azuma et al.

(10) Patent No.: US 6,291,485 B1
(45) Date of Patent: Sep. 18, 2001

(54) 4,5-DIHYDRO-[1H]-BENZ[G]INDAZOLE-3-CARBOXYLIC ACID DERIVATIVES

(75) Inventors: Hiroshi Azuma, 712-1, Ohara Kurihara, Kuki-shi, Saitama 346-0012; Haruo Yamashita, Tachikawa; Katsuyuki Keino, Kawasaki; Shuji Ota, Kawasaki; Takahisa Saito, Kawasaki; Shuichiro Sato, Kawasaki; Hidehisa Hamasaki, Kawasaki; Katsura Suzuki, Kawasaki; Akiko Sugimoto, Hino, all of (JP)

(73) Assignees: Teikoku Hormone Mfg. Co., Ltd., Tokyo; Hiroshi Azuma, Saitama, both of (JP)

( * ) Notice: Subject to any disclaimer, the term of this patent is extended or adjusted under 35 U.S.C. 154(b) by 0 days.

(21) Appl. No.: 09/462,413
(22) PCT Filed: Jun. 22, 1998
(86) PCT No.: PCT/JP98/02758
  § 371 Date: Jan. 10, 2000
  § 102(e) Date: Jan. 10, 2000
(87) PCT Pub. No.: WO99/02519
  PCT Pub. Date: Jan. 21, 1999

(30) Foreign Application Priority Data

Jul. 10, 1997 (JP) ................................. 9-199128

(51) Int. Cl.⁷ .................................................. A01N 43/40
(52) U.S. Cl. .......................................................... 514/333
(58) Field of Search .................. 514/256; 544/333, 544/335, 296, 295

(56) References Cited

FOREIGN PATENT DOCUMENTS

| | | |
|---|---|---|
| 0510526 | 12/1996 | (EP). |
| 9-501920 | 2/1997 | (JP). |
| 9-67352 | 3/1997 | (JP). |
| 9-71570 | 3/1997 | (JP). |
| 9-110840 | 4/1997 | (JP). |
| 93/08799 | 5/1993 | (WO). |

OTHER PUBLICATIONS

Hamilton, "The Antiarrhythmic and Antiinflammatory Activity of a Series of Tricyclic Pyrazoles", J. Heterocyclic Chem., 13, 545–553 (1976).

*Primary Examiner*—John M. Ford
(74) *Attorney, Agent, or Firm*—Wenderoth, Lind & Ponack, L.L.P.

(57) ABSTRACT

4,5-Dihydro-[1H]-benz[g]indazole-3-carboxylic acid derivatives represented by the following formula, or their salts, have excellent antagonism to endothelin receptors and are useful as preventives or remedies for diseases such as hypertension, angina pectoris, myocardial infarction, brain infarction, cerebrovascular contraction, renal insufficiency, hepatic dysfunction, arteriosclerosis and post-PTCA restenosis.

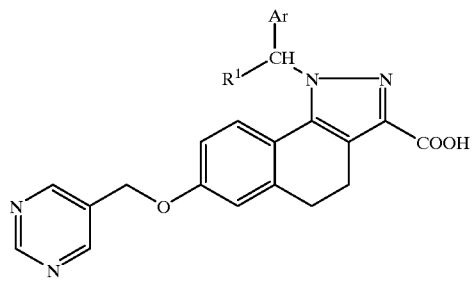

wherein Ar represents an optionally substituted aryl group, and $R^1$ represents a hydrogen atom, an optionally substituted lower alkyl group, an optionally substituted aryl group, an optionally substituted cycloalkyl group or an optionally substituted heterocyclic group.

9 Claims, No Drawings

4,5-DIHYDRO-[1H]-BENZ[G]INDAZOLE-3-CARBOXYLIC ACID DERIVATIVES

CROSS-REFERENCE

This application is a 371 of PCT/JP98/02758 filed Jun. 22, 1998, which is based on Japanese Application No. 199,128/97 filed Jul. 10, 1997.

TECHNICAL FIELD

This invention relates to novel 4,5-dihydro-[1H]-benz[g]-indazole-3-carboxylic acid derivatives. More particularly, it relates to 4,5-dihydro-[1H]-benz[g]-indazole-3-carboxylic acid derivatives represented the following formula, or salts thereof.

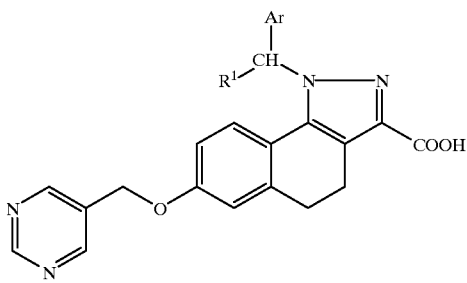

(I)

wherein Ar represents an optionally substituted aryl group, and $R^1$ represents a hydrogen atom, an optionally substituted lower alkyl group, an optionally substituted aryl group, an optionally substituted cycloalkyl group or an optionally substituted heterocyclic group.

BACKGROUND ART

Endothelin is a vasoconstrictive peptide composed of 21 amino acid residues, which was isolated from the culture supernatant of porcine vascular endothelial cells in 1988. This is produced by the processing of an endothelin precursor with an endothelin converting enzyme. Although endothelin is known to be widely produced by the cells of the lungs, intestines, kidneys, pancreas, spleen, heart, eyes, placenta, central nervous system and the like, it is said that endothelin is also produced by many cells other than these cells, such as bronchial epithelial cells, vascular smooth muscle cells and macrophages. As to endothelin, three isopeptides (endohelin-1, endothelin-2 and endothelin-3) are known, and they have a transient vasodilative effect and a subsequent sustained vasoconstrictive effect. Moreover, in addition to their effects on the cardiovascular system, endothelins have a wide variety of effects such as contraction of the airway, intestinal tract and uterine smooth muscle, proliferation of cells, and promotion of aldosterone secretion. It is believed that these effects are achieved through the medium of two subtypes of endothelin receptors (i.e., the endothelin A receptor and the endothelin B receptor). Since an oversecretion of endothelins is considered to be associated with various diseases such as hypertension, ischemic heart diseases, cerebral ischemia, kidney diseases, hepatic dysfunction, arteriosclerosis, and restenosis after percutaneous transluminal coronary angioplasty (i.e., post-PTCA restenosis), compounds having antagonism to endothelin receptors are expected to be effective as remedies for diseases caused by an oversecretion of endothelins.

The conventionally known nonpeptide compounds having antagonism to endothelins include, for example, Bosentan (see EP-A-510526), SB-209670 (see the pamphlet of WO93/8799) and the like. However, these compounds may not be said to be satisfactory.

Moreover, as 4,5-dihydro-[1H]-benz[g]indazole-3-carboxylic acid derivatives, there are known certain 4,5-dihydro-1-phenyl-[1H]-benz[g]indazole-3-carboxylic acids which are substituted by a substituted phenyl group at the 1-position [see J. Heterocyclic Chem., 13, 545 (1976)]. However, neither statement nor suggestion about their antagonism to endothelins is found in this reference.

It has now been found that compounds comprising 4,5-dihydro-[1H]-benz[g]indazole-3-carboxylic acid which is substituted by a 5-pyrimidinylmethoxy group at the 7-position and by a substituted phenylmethyl group at the 1-position have excellent antagonism to endothelin receptors and, moreover, some of these compounds also have an excellent inhibitory effect on phosphodiesterase III.

Thus, the present invention provides 4,5-dihydro-[1H]-benz[g]indazole-3-carboxylic acid derivatives represented by the above formula (I), or their salts.

DISCLOSURE OF THE INVENTION

The term "lower" as used herein means that the radicals or compounds modified by this term have not more than 6 carbon atoms and preferably 1 to 4 carbon atoms.

Thus, examples of the "lower alkyl group" include methyl, ethyl, n-propyl, isopropyl, n-butyl, isobutyl, sec-butyl, tert-butyl and n-hexyl. Examples of the "lower cycloalkyl group" include cycloalkyl groups having 3 to 8 carbon atoms, such as cyclopropyl, cyclopentyl and cyclohexyl. Examples of the "aryl group" include aryl groups having 6 to 14 carbon atoms, such as phenyl, naphthyl and anthryl. Among others, phenyl and naphthyl are preferred.

The "heterocyclic group" may be a monocyclic or polycyclic heterocyclic group which contains 1 to 4 heteroatoms selected from among N, S and O and in which each ring is a four- to eight-membered ring. In such groups, the heterocyclic ring may be a saturated ring or an unsaturated ring (e.g., an aromatic ring), and may be formed by the condensation of a monocyclic hydrocarbon radical with a monocyclic heterocyclic ring. Thus, specific examples of the ring in such heterocyclic groups include pyrrolyl, imidazolyl, pyrazolyl, triazolyl, tetrazolyl, oxazolyl, isoxazolyl, thiazolyl, thiadiazolyl, pyridyl, pyrazinyl, pyrimidinyl, pyridazinyl, benzothienyl, benzofuranyl, indolyl, benzothiazolyl, quinolyl, isoquinolyl, pyridinothiazolyl, pyrrolidinyl and piperidinyl.

Among others, preferred examples of the "heterocyclic group" are monocyclic or bicyclic unsaturated heterocyclic groups which contain 1 to 4 heteroatoms selected from among N, S and O and in which each ring is a five- or six-membered ring. In particular, five- or six-membered monocyclic aromatic heterocyclic groups containing 1 or 2 nitrogen atoms are especially preferred.

The number of substituents in the "optionally substituted aryl group" which can be represented by Ar in the above formula (I) may generally be 0 or from 1 to 5, and preferably from 1 to 3. Preferred examples of the substituents include lower alkyl groups, lower alkoxy groups, halogen-substituted lower alkoxy groups, lower alkoxy-substituted lower alkoxy groups, carboxy-substituted lower alkoxy groups, lower alkylthio groups, lower alkylenedioxy groups, halogen atoms, the hydroxy group, the nitro group and the amino group. As used herein, the "lower alkoxy groups" include, for example, methoxy, ethoxy, n-propoxy, isopropoxy, n-butoxy, sec-butoxy and isopentyloxy. The "lower alkylthio groups" include, for example, methylthio, ethylthio and isopropylthio. The "lower alkylenedioxy groups" include, for example, methylenedioxy, ethylenedioxy and propylenedioxy. It is preferable that these group be attached to two adjacent carbon atoms constituting the ring of the aryl group. The "halogen-substituted lower alkoxy groups" include, for example, trifluoromethoxy and 2,2,2-trifluoroethoxy. The "lower alkoxy-substituted lower alkoxy groups" include, for example, methoxy-methoxy and 2-methoxyethoxy. The "carboxy-substituted lower alkoxy groups" include, for example, carboxymethoxy and 2-carboxy-ethoxy. On the other hand, the halogen atoms include fluorine, chlorine, bromine and like atoms.

The number of substituents in the "optionally substituted alkyl group" which can be represented by $R^1$ in the above formula (I) may generally be 0, 1 or 2, and preferably 1. Preferred examples of the substituents include lower alkoxyl groups, the hydroxy group, and the phenoxy group. Moreover, the number of substituents in the "optionally substituted aryl group" which can be represented by $R^1$ may generally be 0 or from 1 to 5, and preferably from 1 to 3. Preferred examples of the substituents include lower alkyl groups, halogen-substituted lower alkyl groups, lower alkoxy groups, halogen-substituted lower alkoxy groups, aralkyloxy groups, lower alkylene-dioxy groups, halogen atoms and the phenyl group. Moreover, the number of substituents in the "optionally substituted cycloalkyl group" which can be represented by $R^1$ may generally be 0, 1 or 2, and preferably 1. Examples of the substituents include lower alkyl groups and lower alkoxy groups. Furthermore, the number of substituents in the "optionally substituted heterocyclic group" which can be represented by $R^1$ may generally be 0 or from 1 to 3, and preferably 1 or 2. Preferred examples of the substituents include lower alkyl groups, lower alkoxy groups, halogen atoms and the nitro group.

The aforesaid "hydroxy-substituted lower alkyl groups" include, for example, hydroxymethyl and 2-hydroxyethyl. The "phenoxy-substituted lower alkyl groups" include, for example, phenoxymethyl and 2-phenoxyethyl. The "halogen-substituted lower alkyl groups" include, for example, trifluoromethyl and 2,2,2-trifluoroethyl. The "aralkyloxy groups" include, for example, aryl(lower alkyl) oxy groups such as benzyloxy and phenetyloxy.

In the present invention, a particularly preferred class of compounds are those of formula (I) in which Ar represents a phenyl group substituted by one lower alkoxy group.

Another particularly preferred class of compounds are those of formula (I) in which $R^1$ represents a lower alkyl group or a six-membered monocyclic aromatic heterocyclic group containing 1 or 2 nitrogen atoms.

The compounds of formula (I) in accordance with the present invention can form salts. Examples of such salts include alkali metal salts such as sodium, potassium and lithium salts; alkaline earth metal salts such as calcium and magnesium salts; other metallic salts such as aluminum salts; salts formed with an aliphatic or alicyclic amine, such as diethylamine, triethylamine and dicyclohexylamine salts; salts formed with a heterocyclic amine, such as pyrrolidine, piperidine, morpholine, pyridine and picoline salts; and ammonium salts. Among others, pharmaceutically acceptable salts are preferred.

According to the present invention, the compounds of the above formula (I) may be prepared by reacting a compound of the formula

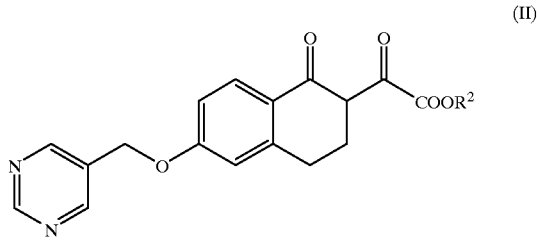

wherein $R^2$ is a lower alkyl group, with a hydrazine derivative of the formula

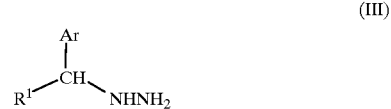

wherein Ar and $R^1$ have the same meanings as described previously, or its hydrate or salt; and hydrolyzing the resulting 4,5-dihydro-[1H]-benz[g]indazole-3-carboxylic acid lower alkyl ester derivative of the formula

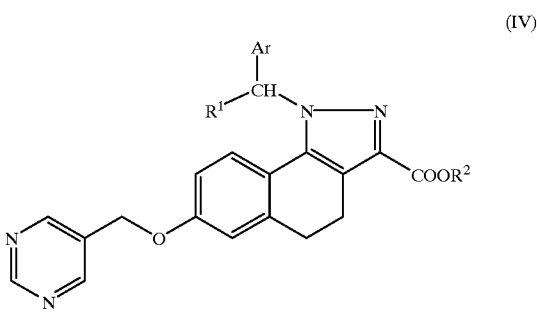

wherein Ar, $R^1$ and $R^2$ have the same meanings as described previously.

The reaction of the compound of the above formula (II) with the hydrazine derivative of the above formula (III), its hydrate or salt may generally be carried out in an inert organic solvent selected, for example, from among alcohols such as methanol and ethanol; ethers such as dioxane and tetrahydrofuran; aromatic hydrocarbons such as benzene, toluene and xylene; carboxylic acids such as acetic acid and propionic acid; and dimethylformamide. As the reaction temperature, it is usually suitable to employ a temperature ranging from room temperature to the reflux temperature of the reaction mixture and preferably from 50° C. to the reflux temperature of the reaction mixture.

The proportion of the hydrazine derivative of formula (III) or its hydrate or salt to the compound of formula (II) may generally be such that the hydrazine derivative or its hydrate or salt is used in an amount of at least 1 mole, preferably 1.05 to 5 moles, and more preferably about 1.1 to 1.5 moles per mole of the compound of formula (II).

Where a free hydrazine derivative or its hydrate is used as the compound of formula (III) in this reaction, it is desirable to use a carboxylic acid (e.g., acetic acid) as the reaction solvent or carry out the reaction in the presence of an acid catalyst (e.g., hydrochloric acid).

Thus, the compound of the above formula (IV) is formed in good yield. This compound may be converted to the compound of the above formula (I) in accordance with the present invention by hydrolysis.

The hydrolysis of the compound of the above formula (IV) may be carried out according to any conventional method for the hydrolysis of esters. For example, this can readily be done by treating the compound of formula (IV) with an alkali (e.g., sodium hydroxide or potassium hydroxide) in a solvent selected, for example, from among alcohols such as methanol and ethanol; ethers such as tetrahydrofuran and dioxane; halogenated hydrocarbons such as chloroform; amides such as dimethylformamide; and mixtures thereof.

Thus, the compound of the above formula (I) desired in the present invention is formed.

The compounds of the above formula (II) which can be used as starting materials in the aforesaid reaction are novel compounds that have not been described in the literature of the prior art. These compounds may be prepared, for example, according to the following reaction scheme 1.

Reaction scheme 1

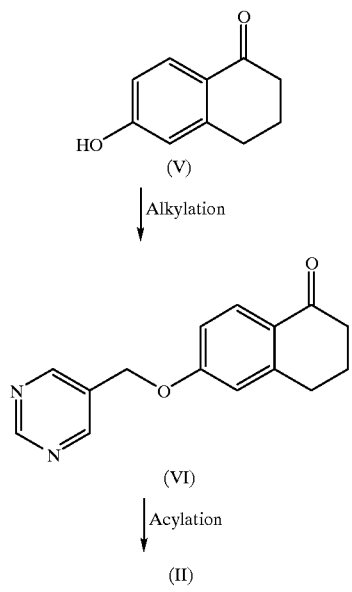

In the above reaction scheme 1, 1-oxo-6-hydroxy-1,2,3,4-tetrahydronaphthalene of formula (V) is first alkylated with 5-chloromethylpyrimidine. This alkylation may be carried out in an inert solvent such as N,N-dimethylformamide, acetone or ethanol, in the presence of a base such as sodium hydride, potassium carbonate or potassium t-butoxide. Then, the resulting 1-oxo-6-(5-pyrimidinylmethoxy)-1,2,3,4-tetrahydronaphthalene of the above formula (VI) may be converted to a compound of formula (II) by treating it with a dialkyl oxalate in an inert solvent such as tetrahydrofuran, methanol, ethanol, isopropanol, benzene, dioxane or dimethylformamide, in the presence of a base such as sodium methoxide, sodium hydride or potassium t-butoxide.

Moreover, most of the compounds of the above formula (III) or their hydrates or salts, which can be used as other starting materials in the aforesaid reaction, are novel compounds that have not been described in the literature of the prior art. These compounds may be prepared, for example, according to the following reaction scheme 2.

Reaction scheme 2

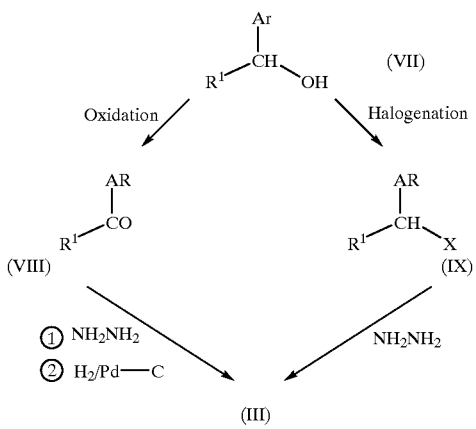

In the above formulae, X represents a halogen atom such as chlorine or bromine, and Ar and $R^1$ have the same meanings as described previously.

Details of the reaction conditions and other information in the above reaction scheme 2 are shown in Examples 30 and 43 which will be given later.

The compounds of the above formula (IV) which can be used in the aforesaid reaction may also be prepared according to a process shown by the following reaction scheme 3.

Reaction scheme 3

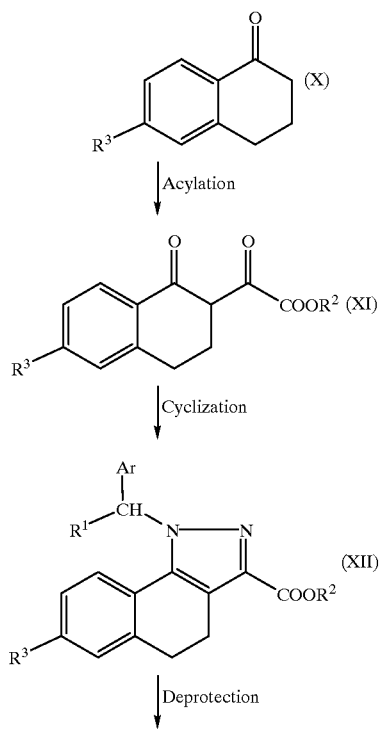

-continued

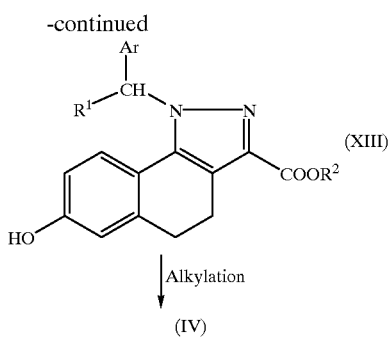

In the above formulae, R³ represents a group which can be converted to a hydroxyl group, such as benzyloxy, and Ar, R¹ and R² have the same meanings as described previously.

Details of the reaction conditions and other information in the above reaction scheme 3 are shown in Example 76 which will be given later.

In the reactions described herein, where the Ar or R¹ group contains a group (e.g., amino, hydroxyl or carboxyl) which may participate in the reactions, it is advantageous to protect that group with a suitable protecting group (e.g., t-butoxycarbonyl for the amino group, methoxymethyl for the hydroxyl group, or methyl ester group for the carboxyl group) and eliminate the protecting group after completion of the reactions.

The compounds of the above formula (I) or their salts, which are formed according to the present invention, may be isolated and purified from the reaction mixture by per se known techniques such as recrystallization, distillation, column chromatography and thin-layer chromatography.

The above-described 4,5-dihydro-[1H]-benz[g]indazole-3-carboxylic acid derivatives represented by formula (I) or their salts in accordance with the present invention have excellent antagonism to endothelin receptors and are useful for the prophylaxis or treatment of diseases associated with an oversecretion of endothelins, such as hypertension, angina pectoris, myocardial infarction, brain infarction, cerebrovascular contraction, renal insufficiency, hepatic dysfunction, arteriosclerosis and post-PTCA restenosis.

Moreover, some of the compounds of formula (I) in accordance with the present invention, such as the compounds of Examples 34 and 70 which will be given later, have an inhibitory effect on phosphodiesterase III in addition to their excellent antagonism to endothelin receptors. Accordingly, among the above-described diseases, they are particularly useful for the prophylaxis or treatment of hypertension, angina pectoris, myocardial infarction and post-PTCA restenosis.

The antagonism to endothelin receptors and the inhibitory effect on phosphodiesterase III, which are possessed by the compounds of formula (I) or their salts in accordance with the present invention, can be measured according to the following procedures.

(1) Measurement of Antagonism to Endothelin Receptors

Among the endothelin (ET) receptor subtypes, the binding of ET to the $ET_A$ and $ET_B$ subtypes was measured by using a crude receptor membrane fraction from the porcine thoracic aorta and a crude receptor membrane fraction from the human placenta, respectively. The tissue (about 40 g) as washed, minced with scissors, and homogenized in 4 volumes of solution A [20 mM HEPES (N-2-hydroxyethylpiperazine-N'-2-ethanesulfonic acid), 3 mM EGTA (ethylene glycol bis(β-aminoethyl ether)-N,N,N',N'-tetraacetic acid), 5 mM EDTA (ethylenediaminetetraacetic acid), 2 μg/ml aprotinin, 3 μg/ml leupeptin, 3 μg/ml pepstatin A, 0.25 mg/ml bacitracin, 0.25 M sucrose] by means of an Ultra-turrax. The resulting homogenate was centrifuged at 8,000 g for 20 minutes, and the supernatant was further centrifuged at 80,000 g for 60 minutes. The precipitate was suspended in solution A and used as a crude receptor membrane fraction, which was divided into portions and stored in a frozen state at −70° C. As a radioligand, 325 Bq of $^{125}$I-ET-1 (81.4 TBq/mmol; manufactured by DuPont-New England Nuclear, Boston, Mss., U.S.A) was placed in a test tube. Then, the crude receptor membrane fraction (20 μg as protein) and a test compound were added thereto. Nonspecific binding was measured by the addition of 125 nM ET-1. The reaction was carried out in solution B [30 mM HEPES, 0.15 M NaCl, 5 mM $MgCl_2$, 0.5 mg/ml bacitracin, 1 mg/ml bovine serum albumin, pH 7.0) at 25° C. for 120 minutes. In order to separate the free radioactive ligand from the membrane-bound one, the reaction mixture was quickly filtered through a glass filter treated with 0.3% polyethyleneimine (GF/C; manufactured by Whatman Inc., U.S.A.) and washed twice with ice-cold solution B. Thereafter, the radioactivity remaining on the filter was measured with a gamma counter.

The results of evaluation of several compounds in accordance with the present invention are shown below.

| Compound | $IC_{50}$ | |
|---|---|---|
| | $ET_A$ receptor | $ET_B$ receptor |
| Example 2 | 31 | 140 |
| Example 14 | 16.8 | 115 |
| Example 34 | 4.5 | 153 |
| Example 41 | 7.4 | 92 |
| Example 70 | 2.5 | 11.3 |

(2) Measurement of an Inhibitory Effect on Phosphodiesterase III

Phosphodiesterase III was prepared according to the method of Frodsham et al. (Eur. J. Pharmacol., Vol. 211, pp. 383–391, 1992).

Specifically, hearts excised from male Hartley strain guinea pigs (400–600 g) were placed in 8 volumes of solution C [10 mM trishydroxymethyl)aminomethane-acetic acid buffer (pH=7.5), 2 mM magnesium chloride, 1 mM dithiothreitol, 2,000 units/ml aprotinin, 50 μM phenylmethylsulfonyl fluoride], minced with scissors, and homogenized three times for 10 seconds by means of a Polytron. The resulting homogenate was centrifuged at 40,000 g for 30 minutes, and the supernatant was applied onto a DEAE-cellulose column and eluted with a linear concentration gradient ranging from 0.2 M to 0.6 M sodium acetate (pH 6.5). The fractions eluted at 0.4–0.5 M were pooled and used as a phosphodiesterase III enzyme fraction.

An inhibitory effect on phosphodiesterase III was measured according to the method of Thompson et al. (Adv. Cycl. Nucl. Res., Vol. 10, p. 69, 1979).

Specifically, a test compound and the phosphodiesterase III enzyme fraction were added to 0.4 ml of a reaction solution [40 mM tris(hydroxymethyl)aminomethane-hydrochloric acid buffer (pH=8.0), 5 mM magnesium chloride, 1 mM dithiothreitol, 0.1 μM [³H] cAMP]. This mixture was reacted at 30° C. for 10 minutes. After completion of the reaction, 5'-nuclease was added thereto so as to convert [³H] 5'-AMP, which was the reaction product with phosphodiesterase III, to [³H] adenosine. Then, the [³H] cAMP and [³H] adenosine present in the reaction mixture were separated with the aid of an anion exchanger. The radioactivity of the latter was measured with a liquid scintillation counter, and the inhibitory effect on phosphodiesterase III was calculated.

The results of evaluation of several compounds in accordance with the present invention are shown below.

| Compound | $IC_{50}$ (nM) |
|---|---|
| Example 34 | 75 |
| Example 70 | 580 |

Thus, the compounds of the above formula (I) or their salts in accordance with the present invention are useful as endothelin receptor antagonists and can hence be used for purposes of therapy or treatment in human and other mammals by oral administration or parenteral administration (e.g., intramuscular injection, intravenous injection, intrarectal administration or percutaneous administration).

When the compounds of the present invention are used as drugs, they may be formed into any of various pharmaceutical preparations according to the intended purpose. These pharmaceutical preparations include solid preparations (e.g., tablets, hard capsules, soft capsules, granules, powders, fine subtilaes, pills and troches), semisolid preparations (e.g., suppositories and ointments), and liquid preparations (e.g., injections, emulsions, suspensions, lotions and sprays). Nontoxic adjuvants which can be used in the aforesaid pharmaceutical preparations include, for example, starch, gelatin, glucose, lactose, fructose, maltose, magnesium carbonate, talc, magnesium stearate, methylcellulose, carboxymethylcellulose and salts thereof, acacia, polyethylene glycol, alkyl esters of p-hydroxybenzoic acid, syrup, ethanol, propylene glycol, petrolatum, carbowax, glycerin, sodium chloride, sodium sulfite, sodium phosphate and citric acid. The aforesaid pharmaceutical preparations may also contain other therapeutically useful drugs.

The content of the compounds of the present invention in the aforesaid pharmaceutical preparations may vary according to the dosage form. Generally, it is desirable that solid and semisolid preparations contain the compounds of the present invention at a concentration of 0.1 to 50% by weight and liquid preparations contain them at a concentration of 0.05 to 10% by weight.

The dosage of the compounds of the present invention may vary widely according to the type of the mammal (including human) to be treated, the route of administration, the severity of symptoms, the diagnosis made by the doctor, and the like. Generally, they may be administered in a daily dose of 0.05 to 100 mg/kg and preferably 0.1 to 50 mg/kg. However, it is a matter of course that they may be administered in doses less than the lower limit of the aforesaid range or greater than the upper limit thereof, depending on the severity of symptoms in the patient and the diagnosis made by the doctor. The aforesaid daily dose may be given at a time or in several divided doses.

EXAMPLES

The present invention is more specifically explained with reference to the following examples and preparation examples.

Example 1

A. Synthesis of 5-chloromethylpyrimidine

Benzoyl peroxide (6 g, 0.025 mol) was added to a mixture of 5-methylpyrimidine (60 g, 0.637 mol), N-chlorosuccinimide (115 g, 0.861 mol) and carbon tetrachloride (1.5 l), and this mixture was heated under reflux for 20 hours. After it was allowed to cool, insoluble matter was filtered off and washed with a small amount of carbon tetrachloride. The filtrate was concentrated under reduced pressure. The resulting oily material was subjected to chromatography on silica gel (1 kg) using ethyl acetate-hexane (1: 2), and eluted with ethyl acetate-hexane (1:2) and then with ethyl acetate to obtain the desired compound (31.2 g, 38%) as an oily material. Since this compound was unstable, it was immediately used in the following reaction.

$^1$HNMR (CDCl$_3$): δ 9.20 (s, 1H), 8.79 (s, 2H), 4.59 (s, 2H).

B. Synthesis of 1-oxo-6-(5-pyrimidinylmethoxy)-1, 2,3,4-tetrahydronaphthalene

While a mixture of 1-oxo-6-hydroxy-1,2,3,4-tetrahydronaphthalene (38 g, 0.234 mol), potassium carbonate (48 g, 0.347 mol) and N,N-dimethylformamide (250 ml) was warmed at 60° C. with stirring, a mixture of the compound (31 g, 0.241 mol) obtained in the above step A and N,N-dimethylformamide (25 ml) was added drop-wise thereto. This mixture was stirred at the same temperature for 18 hours. Insoluble matter was filtered off and washed with N,N-dimethylformamide (50 ml) and then with chloroform (2×150 ml). The solvent was distilled off from the N,N-dimethylformamide filtrate under reduced pressure, the resulting crystalline residue was dissolved in the previous chloroform washings. After the addition of chloroform (300 ml), this solution was washed with water (2×200 ml) and dried (over magnesium sulfate). The chloroform solution was subjected to chromatography on silica gel (500 g), and eluted with chloroform-methanol (100:1) and then with chloroform-methanol (10:1) to obtain a pale-yellow solid. This solid was crystallized from ethyl acetate to obtained the desired compound (55.7 g, 93%) as pale-yellow crystals.

Melting point: 146.5–147° C.; $^1$HNMR (CDCl$_3$): δ 9.23 (s, 1H), 8.83 (s, 2H), 8.05 (d, J=8.6, 1H), 6.90 (dd, J=2.5, 8.6, 1H), 6.80 (d, J=2.5, 1H), 5.14 (s, 2H), 2.94 (t, J=5.9, 2H), 2.62 (dd, J=5.5, 6.8, 2H), 2.35–1.95 (m, 2H).

C. Synthesis of 1-oxo-6-(5-pyrimidinylmethoxy)-1, 2,3,4-tetrahydronaphtho-2-glyoxylic acid methyl ester Methanol was distilled off from a methanolic solution of sodium methoxide (28%, 62.7 g, 0.33 mol) under reduced pressure, and the resulting residue was suspended in anhydrous tetrahydrofuran (800 ml). While this suspension was stirred under cooling with ice in an atmosphere of argon, a mixture of the compound (55.0 g, 0.22 mol) obtained in the above step B, dimethyl oxalate (33.3 g, 0.282 mol) and anhydrous tetrahydrofuran (1,600 ml) was added thereto at a time. This mixture was stirred at room temperature for 1 hour. After 1 N hydrochloric acid (325 ml) and a saturated aqueous solution of sodium chloride (500 ml) were added to the reaction mixture, the reaction mixture was allowed to separate. After the organic layer was dried (over magnesium sulfate), the solvent was distilled off under reduced pressure. The resulting solid was crystallized from methanol to obtain the desired compound (62.8 g, 85%) as pale-yellow crystals.

Melting point: 136.5–137.5° C.; $^1$HNMR (CDCl$_3$): δ 15.85 (s, 1H), 9.24 (s, $^1$H), 8.84 (s, 2H), 8.04 (d, J=8.5, 1H), 6.95 (dd, J=2.5, 8.5, 1H), 6.82 (d, J=2.5, 1H), 5.16 (s, 2H), 3.91 (s, 3H), 3.15–2.85 (m, 4H).

D. Synthesis of 1-benzyl-4,5-dihydro-7-(5-pyrimidinylmethoxy)-[1H]-benz[g]indazole-3-carboxylic acid methyl ester The compound (170 mg, 0.5 m mol) obtained in the above step C was dissolved in acetic acid (3 ml). After the addition of benzylhydrazine hydrochloride (88 mg, 0.55 m mol), this mixture was stirred at 60° C. overnight. After the addition of ice water (30 ml), the reaction mixture was alkalified with 25% aqueous ammonia (4 ml) and then extracted with chloroform (2×20 ml). After the combined extract was washed with water (2×30 ml) and dried (over magnesium sulfate), the solvent was distilled off under reduced pressure. The resulting solid was crystallized from chloroform-methanol to obtain the desired compound (169 mg, 70%) as colorless crystals.

Melting point: 202–203° C.; $^1$HNMR (CDCl$_3$): δ 9.21 (s, 1H), 8.81 (s, 2H), 7.45–6.90 (m, 7H), 6.72 (dd, J=2.6, 8.4, 1H), 5.71 (s, 2H), 5.06 (s, 2H), 3.95 (s, 3H), 3.20–2.80 (m, 4H).

E. Synthesis of 1-benzyl-4,5-dihydro-7-(5-pyrimidinylmethoxy)-[1H]-benz[g]indazole-3-carboxylic acid The compound (230 mg, 0.54 m mol) obtained in the above step D was dissolved in tetrahydrofuran (30 ml). After the addition of 2 N sodium hydroxide (3 ml), this mixture was stirred overnight. After 2 N sodium hydroxide (2 ml) was added thereto and the stirring was continued for another 24 hours, the reaction mixture was acidified with 5 N hydrochloric acid (3 ml). Water (20 ml) was added thereto, and this solution was extracted with ethyl acetate (2×20 ml). After the combined organic layer was washed with water (2×20 ml) and dried, the solvent was distilled off under reduced pressure. The resulting solid was washed with methanol to obtain the desired compound (206 mg, 92%) as a colorless solid.

Melting point: 235.5–237° C.; $^1$HNMR (DMSO-d$_6$): δ 12.50 (br. s, 1H), 9.16 (s, 1H), 8.88 (s, 2H), 7.50–6.95 (m, 7H), 6.87 (dd, J=2.5, 8.5, 1H), 5.73 (s, 2H), 5.18 (s, 2H), 2.88 (br. s, 4H). Elemental analysis (as C$_{24}$H$_{20}$N$_4$O$_3$); Calculated value (%): C 69.89, H 4.89, N 13.58. Observation value (%): C 69.80, H 4.80, N 13.58.

Example 2

A. Synthesis of 3-methoxybenzylhydrazine

While a solution of hydrazine monohydrate (10 g, 0.2 mol) in ethanol (35 ml) was heated under reflux, a solution of 3-methoxybenzyl chloride (5.0 g, 32 m mol) in ethanol (15 ml) was added drop-wise thereto over a period of 30 minutes. After this mixture was further refluxed for 2 hours, the solvent was distilled off under reduced pressure. The oily residue was extracted with ether (2×30 ml). After the extract was dried, the solvent was distilled off under reduced pressure. The resulting residue was subjected to chromatography on silica gel (40 g) using chloroform-methanol (20:1), so that there was obtained a crude fraction containing the desired compound. Then, this crude fraction was distilled (120–123° C./1–2 mmHg) to obtain the desired compound (2.9 g, 60%) as a colorless oily material.

B. Synthesis of 4,5-dihydro-1-(3-methoxybenzyl)-7-(5-pyrimidinylmethoxy)-[1H]-benz[g]indazole-3-carboxylic acid methyl ester 1-Oxo-6-(5-pyrimidinylmethoxy)-1,2,3,4-tetrahydronaphth o-2-glyoxylic acid methyl ester (340 mg, 1 m mol) was dissolved in acetic acid (10 ml). After the addition of the compound (190 mg, 1.25 m mol) obtained in the above step A, this mixture was stirred at 60° C. for 3 hours. After the addition of ice water (50 ml), the reaction mixture was alkalified with 25% aqueous ammonia (15 ml) and then extracted with chloroform (2×40 ml). After the combined extract was washed with water (2×30 ml) and dried, the solvent was distilled off under reduced pressure. The residue was dissolved in a small amount of chloroform and subjected to chromatography on silica gel (50 g) using ethyl acetate. The resulting solid was crystallized from chloroform-methanol to obtain the desired compound (300 mg, 65%) as colorless crystals.

Melting point: 184–184.5° C.; $^1$HNMR (DMSO-d$_6$): δ 9.24 (s, 1H), 8.88 (s, 2H), 7.35–7.15 (m, 2H), 7.00–6.60 (m, 5H), 5.67 (s, 2H), 5.10 (s, 2H), 3.95 (s, 3H), 3.75 (s, 3H), 3.25–2.75 (m, 4H).

C. Synthesis of 4,5-dihydro-1-(3-methoxybenzyl)-7-(5-pyrimidinylmethoxy)-[1H]-benz[g]indazole-3-carboxylic acid The compound (195 mg, 0.43 m mol) obtained in the above step B was dissolved in a mixture of tetrahydrofuran (20 ml) and methanol (10 ml). After the addition of 2 N sodium hydroxide (5 ml), this mixture was stirred for 48 hours. After the reaction mixture was acidified with 1 N hydrochloric acid (12 ml), the tetrahydrofuran and methanol were distilled off. After water was added to the residue, the precipitated solid was separated by filtration, and washed successively with water and methanol. This solid was dried in vacuo to obtain the desired compound (152 mg, 80%) as a colorless solid.

Melting point: 220–221° C.; $^1$HNMR (DMSO-d6): δ 12.65 (br. s, 1H), 9.14 (s, 1H), 8.87 (s, 2H), 7.38 (d, J=8.8, 1H), 7.20 (d, J=7.9, 1H), 7.06 (d, J=2.4, 1H), 7.00–6.50 (m, 4H), 5.68 (s, 2H), 5.18 (s, 2H), 3.70 (s, 3H), 2.89 (s, 4H). Elemental analysis (as C$_{25}$H$_{22}$N$_4$O$_4$); Calculated value (%): C 67.86, H 5.01, N 12.66. Observation value (%): C 67.62, H 4.90, N 12.54.

Examples 3 to 26

Substituted benzyl halides were treated in the same manner as in Example 2 to obtain the compounds shown in Tables 1, 2 and 3.

TABLE 1

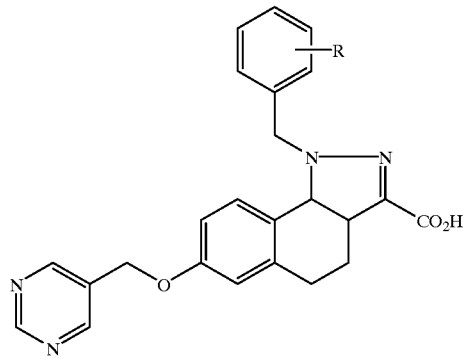

| Example | R | melting point (° C.) | ¹HNMR (DMSO-$d_6$) (δ) |
|---|---|---|---|
| Example 3 | o-Methoxy | 250.5–255 (dec.) | 12.60 (br.s, 1H), 9.15 (s, 1H), 8.87 (s, 2H), 7.40–6.70 (m, 6H), 6.52 (dd, J = 1.3, 7.5, 1H), 5.59 (s, 2H), 5.18 (s, 2H), 3.89 (s, 3H), 2.89 (s, 3H) |
| Example 4 | p-Methoxy | 222.5–224.5 | 12.60 (br.s, 1H), 9.15 (s, 1H), 8.88 (s, 2H), 7.43 (d, J = 8.6, 1H), 7.15–6.80 (m, 6H), 5.64 (s, 2H), 5.18 (s, 2H), 3.71 (s, 3H), 2.87 (s, 3H) |
| Example 5 | o-Methyl | 260.5–262.5 | 12.60 (br.s, 1H), 9.15 (s, 1H), 8.87 (s, 2H), 7.40–7.00 (m, 5H), 7.00–6.75 (m, 1H), 6.50–6.30 (m, 1H), 5.67 (s, 2H), 5.17 (s, 2H), 2.91 (s, 4H), 2.37 (s, 3H) |
| Example 6 | m-Methyl | 232.5–235 | 12.65 (br.s, 1H), 9.16 (s, 1H), 8.89 (s, 2H), 7.38 (d, J = 8.6, 1H), 7.30–6.70 (m, 6H), 5.68 (s, 2H), 5.19 (s, 2H), 2.88 (s, 4H), 2.26 (s, 3H) |
| Example 7 | p-Methyl | 252.5–256.5 (dec.) | 12.65 (br.s, 1H), 9.16 (s, 1H), 8.89 (s, 2H), 7.40 (d, J = 8.6, 1H), 7.25–6.75 (m, 6H), 5.67 (s, 2H), 5.18 (s, 2H), 2.87 (s, 4H), 2.26 (s, 3H) |
| Example 8 | o-Chloro | 267.5–269 (dec.) | 9.15 (s, 1H), 8.87 (s, 2H), 7.65–6.75 (m, 6H), 6.60–6.40 (m, 1H), 5.70 (s, 2H), 5.16 (s, 2H), 2.90 (s, 4H) |
| Example 9 | m-Chloro | 241–244.5 | 12.70 (br.s, 1H), 9.16 (s, 1H), 8.89 (s, 2H), 7.50–7.25 (m, 3H), 7.25–6.80 (m, 4H), 5.76 (s, 2H), 5.20 (s, 2H), 2.89 (s, 4H) |
| Example 10 | p-Chloro | 266.5–273 (dec.) | 12.53 (br.s, 1H), 9.16 (s, 1H), 8.89 (s, 2H), 7.50–7.25 (m, 3H), 7.20–7.00 (m, 3H), 6.88 (dd, J = 2.4, 8.6, 1H), 5.73 (s, 2H), 5.19 (s, 2H), 2.88 (s, 4H) |
| Example 11 | o-Nitro | 258–265 (dec.) | 12.70 (br.s, 1H), 9.15 (s, 1H), 8.87 (s, 2H), 8.35–8.10 (m, 1H), 7.85–7.45 (m, 2H), 7.30–7.00 (m, 2H), 7.00–6.55 (m, 2H), 6.08 (s, 2H), 5.18 (s, 2H), 2.92 (s, 4H) |
| Example 12 | m-Nitro | 270.5–272 | 12.80 (br.s, 1H), 9.16 (s, 1H), 8.88 (s, 2H), 8.25–7.90 (m, 2H), 7.80–7.30 (m, 3H), 7.20–7.00 (m, 1H), 7.00–6.75 (m, 1H), 5.91 (s, 2H), 5.19 (s, 2H), 2.90 (s, 4H) |
| Example 13 | p-Nitro | 269–271.5 | 9.15 (s, 1H), 8.88 (s, 2H), 8.35–8.35 (m, 2H), 7.50–7.20 (m, 3H), 7.20–6.95 (m, 1H), 6.86 (dd, J = 2.6, 8.6, 1H), 5.91 (s, 2H), 5.18 (s, 2H), 2.90 (s, 4H) |

TABLE 2

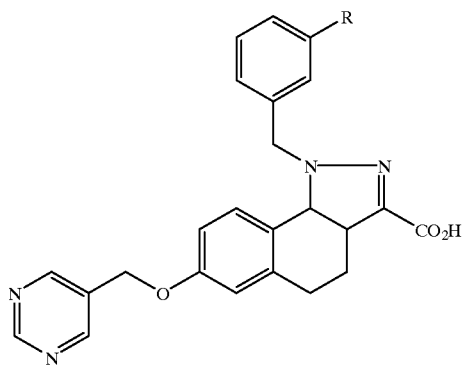

| Example | R | melting point (° C.) | ¹HNMR (DMSO-$d_6$) (δ) |
|---|---|---|---|
| Example 14 | Ethoxy | 218–220 | 9.16 (s, 1H), 8.89 (s, 2H), 7.39 (d, J = 8.6, 1H), 7.30–6.50 (m, 6H), 5.68 (s, 2H), 5.19 (s, 2H), 3.96 (q, J = 7.0, 2H), 2.88 (s, 4H), 1.27 (t, J = 7.0, 3H) |
| Example 15 | Propoxy | 200.5–203 | 9.16 (s, 1H), 8.88 (s, 2H), 7.39 (d, J = 8.6, 1H), 7.30–6.50 (m, 6H), 5.68 (s, 2H), 5.19 (s, 2H), 3.86 (t, J = 6.5, 2H), 2.89 (s, 4H), 1.90–1.45 (m, 2H), 0.93 (t, J = 7.0, 3H) |
| Example 16 | Isopropoxy | 212–215 | 9.16 (s, 1H), 8.89 (s, 2H), 7.55–6.50 (m, 7H), 5.68 (s, 2H), 5.19 (s, 2H), 4.70–4.35 (m, 1H), 2.88 (s, 4H), 1.20 (d, J = 6.0, 6H) |

TABLE 2-continued

| Example | R | melting point (° C.) | ¹HNMR (DMSO-$d_6$) (δ) |
|---|---|---|---|
| Example 17 | Methoxymethoxy | 211.5–215.5 | 9.16 (s, 1H), 8.89 (s, 2H), 7.40 (d, J = 8.6, 1H), 7.30–6.60 (m, 6H), 5.70 (s, 2H), 5.19 (s, 2H), 5.12 (s, 2H), 3.33 (s, 3H), 2.89 (s, 4H) |
| Example 18 | Methylthio | 225.5–230.5 (dec.) | 9.16 (s, 1H), 8.89 (s, 2H), 7.60–6.65 (m, 7H), 5.71 (s, 2H), 5.19 (s, 2H), 2.89 (s, 4H), 2.40 (s, 3H) |

TABLE 3

| Example | R | melting point (° C.) | ¹HNMR (DMSO-$d_6$) (δ) |
|---|---|---|---|
| Example 19 | 2,3-Dimethoxyphenyl | 203–205.5 | 9.16 (s, 1H), 8.88 (s, 2H), 7.28 (d, J = 8.6, 1H), 7.15–6.70 (m, 4H), 6.16 (dd, J = 3.5, 5.7, 1H), 5.64 (s, 2H), 5.18 (s, 2H), 3.83 (s, 3H), 3.80 (s, 3H), 2.88 (s, 4H) |
| Example 20 | 3,4-Dimethoxyphenyl | 218.5–221 | 12.60 (br.s, 1H), 9.16 (s, 1H), 8.89 (s, 2H), 7.45 (d, J = 8.6, 1H), 7.07 (d, J = 2.4, 1H), 7.00–6.75 (m, 3H), 6.49 (dd, J = 1.9, 8.2, 1H), 5.63 (s, 2H), 5.19 (s, 2H) 3.70 (s, 3H), 3.69 (s, 3H), 2.87 (s, 4H) |
| Example 21 | 3,5-Dimethoxyphenyl | 224–228.5 | 12.65 (br.s, 1H), 9.16 (s, 1H), 8.89 (s, 2H), 7.40 (d, J = 8.6, 1H), 7.15–6.80 (m, 3H), 6.38 (t, J = 2.2, 1H), 6.21 (d, J = 2.2, 2H), 5.64 (s, 2H), 5.19 (s, 2H), 3.67 (s, 6H), 2.88 (s, 4H) |
| Example 22 | 2,5-Dimethoxyphenyl | 208.5–211 | 12.65 (br.s, 1H), 9.16 (s, 1H), 8.89 (s, 2H), 7.26 (d, J = 8.4, 1H), 7.20–6.75 (m, 4H), 6.07 (d, J = 2.6, 1H), 5.57 (s, 2H), 5.19 (s, 2H), 3.83 (s, 3H), 3.56 (s, 3H), 2.89 (s, 4H) |
| Example 23 | 1-Naphthyl | 280–283 (dec.) | 9.14 (s, 1H), 8.84 (s, 2H), 8.30–7.05 (m, 8H), 6.85–6.50 (m, 2H), 6.19 (s, 2H), 5.12 (s, 2H), 2.94 (s, 4H) |
| Example 24 | 2-Naphthyl | 270–271.5 (dec.) | 12.70 (br.s, 1H), 9.15 (s, 1H), 8.86 (s, 2H), 8.00–7.75 (m, 3H), 7.65–7.20 (m, 5H), 7.06 (d, J = 2.5, 1H), 6.85 (dd, J = 2.5, 8.5, 1H), 5.90 (s, 2H), 5.15 (s, 2H), 2.91 (s, 4H) |
| Example 25 | 2,3-Methylenedioxyphenol | 284.5–285.5 (dec.) | 9.17 (s, 1H), 8.90 (s, 2H), 7.43 (d, J = 8.4, 1H), 7.15–6.70 (m, 4H), 6.40–6.25 (m, 1H), 6.08 (s, 2H), 5.63 (s, 2H), 5.20 (s, 2H), 2.87 (s, 4H) |
| Example 26 | 3,4-Methylenedioxyphenyl | 263.5–267 (dec.) | 9.16 (s, 1H), 8.89 (s, 2H), 7.44 (d, J = 8.6, 1H), 7.20–6.45 (m, 5H), 5.92 (s, 2H), 5.61 (s, 2H), 5.20 (s, 2H), 2.87 (s, 4H) |

Example 27

A. Synthesis of 4,5-dihydro-1-(3-methoxymethoxybenzyl)-7-(5-pyrimidinylmethoxy)-[1H]-benz[g]indazole-3-carboxylic acid methyl ester 3-Methoxymethoxybenzylhydrazine and 1-oxo-6-(5-pyrimidinylmethoxy)-1,2,3,4-tetrahydronaphtho-2-glyoxylic acid methyl ester were treated in the same manner as in the step B of Example 2. Thus, the desired compound was obtained as colorless crystals.

Melting point: 178–180.5° C.; ¹HNMR (CDCl$_3$): δ 9.21 (s, 1H), 8.80 (s, 2H), 7.35–7.10 (m, 2H), 7.05–6.60 (m, 5H), 5.67 (s, 2H), 5.12 (s, 2H), 5.07 (s, 2H), 3.95 (s, 3H), 3.43 (s, 3H), 3.20–2.80 (m, 4H).

B. Synthesis of 4,5-dihydro-1-(3-methoxymethoxybenzyl)-7-(5-pyrimidinylmethoxy)-[1H]-benz[g]indazole-3-carboxylic acid The compound obtained in the above step A was hydrolyzed in the same manner as in the step C of Example 2. Thus, the desired compound (the compound of Example 17) was obtained as a colorless solid.

Elemental analysis (as $C_{26}H_{24}N_4O_5$); Calculated value (%): C 66.09, H 5.12, N 11.86. Observation value (%): C 65.79, H 5.03, N 11.74.

C. Synthesis of 4,5-dihydro-1-(3-hydroxybenzyl)-7-(5-pyrimidinylmethoxy)-[1H]-benz[g]indazole-3-carboxylic acid 6 N hydrochloric acid (2 ml) was added to a solution in tetrahydrofuran (10 ml) of the compound (110 mg, 0.23 m mol) obtained in the above step B, and this mixture was stirred at room temperature for 2 hours. After the solvent was distilled off and ice water (50 ml) was added to the residue, the precipitated solid was separated by filtration and washed with water and ethyl acetate. The solid was dried in vacuo to obtain the desired compound (88 mg, 88%) as a colorless solid.

Melting point: 251–255.5° C.; $^1$HNMR (DMSO-$d_6$): δ 12.65 (br. s, 1H), 9.38 (s, 1H), 9.16 (s, 1H), 8.89 (s, 2H), 7.37 (d, J=8.4, 1H), 7.30–6.80 (m, 3H), 6.75–6.35 (m, 3H), 5.63 (s, 2H), 5.19 (s, 2H), 2.89 (s, 4H). Elemental analysis (as $C_{24}H_{20}N_4O_4 \cdot 1/4H_2O$); Calculated value (%): C 66.58, H 4.77, N 12.94. Observation value (%): C 66.51, H 4.61, N 12.78.

Example 28

A. Synthesis of 4,5-dihydro-1-(3-hydroxybenzyl)-7-(5-pyrimidinylmethoxy)-[1H]-benz[g]indazole-3-carboxylic acid methyl ester 6 N hydrochloric acid (3 ml) was added to a solution in tetrahydrofuran (15 ml) of the 4,5-dihydro-1-(3-methoxymethoxybenzyl)-7-(5-pyrimidinylmethoxy)-[1H]-benz[g]indazole-3-carboxylic acid methyl ester (308 mg, 0.63 m mol) obtained in the step A of Example 27, and this mixture was stirred at room temperature for 3 hours. Thereafter, the reaction mixture was concentrated under reduced pressure. After the addition of ice water (50 ml), the reaction mixture was alkalified with a saturated aqueous solution of sodium bicarbonate and then extracted with chloroform (2×50 ml). After the extract was washed with water and dried, the solvent was distilled off under reduced pressure. The resulting solid residue was washed with ethyl acetate to obtain the desired compound (187 mg, 66%) as a pale-yellow solid.

Melting point: 217.5–221.5° C.; $^1$HNMR (CDCl$_3$): δ 9.20 (s, 1H), 8.80 (s, 2H), 7.44 (br. s, 1H), 7.35–7.05 (m, 2H), 7.05–6.60 (m, 4H), 6.50–6.30 (m, 1H), 5.59 (s, 2H), 5.07 (s, 2H), 3.49 (s, 3H), 3.30–2.70 (m, 4H).

B. Synthesis of 4,5-dihydro-1-(3-methoxycarbonylmethoxybenzyl)-7-(5-pyrimidinylmethoxy)-[1H]-benz[g]indazole-3-carboxylic acid methyl ester Methyl chloroacetate (40 mg, 0.37 m mol) was added to a solution in N,N-dimethylformamide (5 ml) of the compound (150 mg, 0.34 m mol) obtained in the above step A and potassium carbonate (52 mg, 0.37 m mol), and this mixture was stirred at 60° C. for 2.5 hours. Thereafter, the reaction mixture was concentrated under reduced pressure. After the addition of ice water (50 ml), the reaction mixture was extracted with chloroform (2×30 ml). After the extract was washed with water and dried, the solvent was distilled off under reduced pressure. The resulting solid residue was washed with ether to obtain the desired compound (149 mg, 85%) as a colorless solid.

Melting point: 183.5–186.5° C.; $^1$HNMR (CDCl$_3$): δ 9.21 (s, 1H), 8.80 (s, 2H), 7.40–7.05 (m, 2H), 7.05–6.65 (m, 5H), 5.67 (s, 2H), 5.07 (s, 2H), 4.56 (s, 2H), 3.95 (s, 3H), 3.75 (s, 3H), 3.20–2.80 (m, 4H).

C. Synthesis of 1-(3-carbonylmethoxybenzyl)-4,5-dihydro-7-(5-pyrimidinylmethoxy)-[1H]-benz[g]indazole-3-carboxylic acid The compound (120 mg, 0.23 m mol) obtained in the above tep B was hydrolyzed in the same manner as in the step C of Example 2. Thus, the desired compound (98 mg, 86%) was obtained as a colorless solid.

Melting point: 280–281° C.; $^1$HNMR (DMSO-$d_6$): δ 12.69 (br. s, 1H), 9.16 (s, 1H), 8.89 (s, 2H), 7.50–6.50 (m, 7H), 5.69 (s, 2H), 5.19 (s, 2H), 4.61 (s, 2H), 2.88 (s, 4H). Elemental analysis (as $C_{26}H_{22}N_4O_6 \cdot 1/4H_2O$); Calculated value (%): C 63.60, H 4.62, N 11.41. Observation value (%): C 63.68, H 4.45, N 11.22.

Example 29

A. Synthesis of 3-tert-butoxycarbonylaminobenzylhydrazine

While a solution of hydrazine monohydrate (1.32 g, 26.4 m mol) in ethanol (20 ml) was heated under reflux, a solution of 3-tert-butoxycarbonylaminobenzyl chloride (1.06 g, 4.4 m mol) in ethanol (10 ml) was added dropwise thereto over a period of 5 minutes. After this mixture was further refluxed for 0.5 hour, the solvent was distilled off under reduced pressure. The resulting oily residue was extracted with ether (2×20 ml). After the extract was concentrated under reduced pressure, the resulting residue was subjected to chromatography on silica gel (50 g) using chloroform-methanol (10:1), so that the desired compound (0.91 g, 87%) was obtained as an oily material.

$^1$HNMR (CDCl$_3$): δ 7.60–6.85 (m, 4H), 6.66 (br. s, 1H), 3.88 (s, 2H), 3.54 (br. s, 3H), 1.52 (s, 9H).

B. Synthesis of 1-(3-tert-butoxycarbonylaminobenzyl)-4,5-dihydro-7-(5-pyrimidinylmethoxy)-[1H]-benz[g]indazole-3-carboxylic acid methyl ester The compound (900 mg, 3.8 m mol) obtained in the above step A and 1-oxo-6-(5-pyrimidinylmethoxy)-1,2,3,4-tetrahydro-naphth o-2-glyoxylic acid methyl ester were treated in the same manner as in the step B of Example 2. Thus, the desired compound (577 mg, 70%) was obtained as colorless crystals.

Melting point: 221–222.5° C.; $^1$HNMR (CDCl$_3$): δ 9.21 (s, 1H), 8.80 (s, 2H), 7.45–6.85 (m, 4H), 6.85–6.65 (m, 2H), 6.50–6.35 (m, 1H), 5.66 (s, 2H), 5.06 (s, 2H), 3.95 (s, 3H), 3.20–2.85 (m, 4H), 1.50 (s, 9H).

C. Synthesis of 1-(3-tert-butoxycarbonylaminobenzyl)-4,5-dihydro-7-(5-pyrimidinylmethoxy)-[1H]-benz[g]indazole-3-carboxylic acid The compound (120 mg, 0.22 m mol) obtained in the above step B was hydrolyzed in the same manner as in the step C of Example 2. Thus, the desired compound (103 mg, 88%) was obtained as a colorless solid.

Melting point: 225.5–226.5° C.; $^1$HNMR (DMSO-$d_6$): δ 9.15 (s, 1H), 8.87 (s, 2H), 7.50–7.00 (m, 5H), 7.00–6.75 (m, 1H), 6.75–6.50 (m, 1H), 5.65 (s, 2H), 5.18 (s, 2H), 2.89 (s, 4H), 1.44 (s, 9H).

D. Synthesis of 1-(3-aminobenzyl)-4,5-dihydro-7-(5-pyrimidinylmethoxy)-[1H]-benz[g]indazole-3-carboxylic acid hydrochloride Concentrated hydrochloric acid (1 ml) was added to a solution in ethyl acetate (3 ml) of the compound (65 mg, 0.12 m mol) obtained in the above step C, and this mixture was stirred at room temperature for 3 hours. After the reaction mixture was concentrated under reduced pressure and ice water (30 ml) was added thereto, the precipitated solid was separated by filtration and washed with water. The solid was dried in vacuo to obtain the desired compound (39 mg, 74%) as a colorless solid.

Melting point: 195.5–199° C.; $^1$HNMR (DMSO-$d_6$): δ 9.16 (s, 1H), 8.89 (s, 2H), 7.55–6.70 (m, 7H), 5.74 (s, 2H), 5.19 (s, 2H), 2.89 (s, 4H).

Example 30

A. Synthesis of 3-methoxy-α-methylbenzylhydrazine

A mixture of 3'-methoxyacetophenone (1.5 g, 10 m mol), anhydrous hydrazine (1.28 g, 40 m mol) and dry ethanol (10 ml) was heated under reflux for 3 hours. Thereafter, the solvent was distilled off under reduced pressure. The residue was subjected to chromatography on silica gel (50 g) using ethyl acetate-hexane (1:1), and eluted with ethyl acetate-hexane (1:1) and then with ethyl acetate. The resulting yellow oily material (1.2 g) was dissolved in ethanol (20 ml). After the addition of 5% palladium-carbon (0.5 g), this solution was stirred in an atmosphere of hydrogen (40 kg/cm$^2$) for 48 hours. The catalyst was filtered off, and the filtrate was concentrated under reduced pressure. The resulting residue was subjected to chromatography on silica gel (30 g) using chloroform-methanol (100:1), and eluted with chloroform-methanol (100:1) and then with chloroform-methanol (10:1). Thus, the desired compound (0.68 g, 41%) was obtained as an oily material.

$^1$HNMR (CDCl$_3$): δ 7.30–7.15 (m, 1H), 7.00–6.70 (m, 3H), 4.27 (s, 3H), 3.81 (s, 3H), 3.76 (q, J=6.6, 1H), 1.34 (d, J=6.6, 3H).

B. Synthesis of 4,5-dihydro-1-(3-methoxy-α-methylbenzyl)-7-(5-pyrimidinylmethoxy)-[1H]-benz[g]indazole-3-carboxylic acid methyl ester The compound obtained in the above step A and 1-oxo-6-(5-pyrimidinylmethoxy)-1,2,3,4-tetrahydronaphtho-2-glyoxylic acid methyl ester were treated in the same manner as in the step B of Example 2. Thus, the desired compound was obtained as colorless crystals (60%).

Melting point: 142–146° C.; $^1$HNMR (CDCl$_3$): δ 9.20 (s, 1H), 8.80 (s, 2H), 7.40–7.15 (m, 2H), 7.00–6.65 (m, 5H), 5.87 (q, J=6.8, 1H), 5.07 (s, 2H), 3.95 (s, 3H), 3.75 (s, 3H), 3.35–2.70 (m, 4H), 2.00 (d, J=6.8, 1H).

C. Synthesis of 4,5-dihydro-1-(3-methoxy-α-methylbenzyl)-7-(5-pyrimidinylmethoxy)-[1H]-benz[g]indazole-3-carboxylic acid The compound (230 mg, 0.49 m mol) obtained in the above step B was dissolved in a mixture of tetrahydrofuran (10 ml) and methanol (10 ml). After the addition of 2 N sodium hydroxide (2 ml), this mixture was stirred for 48 hours. After the reaction mixture was acidified with 1 N hydrochloric acid (6 ml), the tetrahydrofuran and methanol were distilled off under reduced pressure. The precipitated solid was separated by filtration and washed with water and methanol. The solid was dried in vacuo to obtain the desired compound (180 mg, 80%) as a colorless solid.

Melting point: 200–201° C.; $^1$HNMR (DMSO-$d_6$): δ 12.60 (br. s, 1H), 9.16 (s, 1H), 8.89 (s, 2H), 7.40 (d, J=8.6, 1H), 7.20 (d, J=7.9, 1H), 7.15–6.60 (m, 5H), 6.06 (q, J=7.0, 1H), 5.20 (s, 2H), 3.71 (s, 3H), 3.20–2.70 (m, 4H), 1.87 (d, J=7.0, 3H). Elemental analysis (as $C_{26}H_{24}N_4O_4$); Calculated value (%): C 68.41, H 5.30, N 12.27. Observation value (%): C 68.14, H 5.22, N 12.27.

Examples 31 to 38

Corresponding starting compounds were treated in the same manner as in Example 30 to obtain the compounds shown in Table 4.

TABLE 4

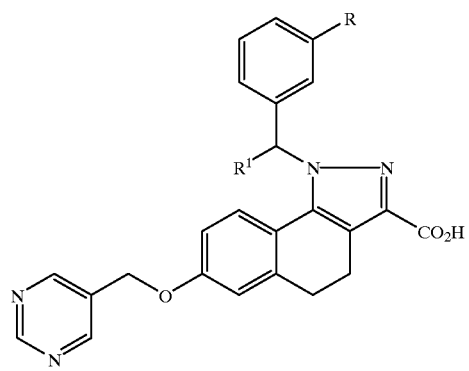

| Example | R | R$^1$ | melting point (° C.) | $^1$HNMR (DMSO-$d_6$) (δ) |
|---|---|---|---|---|
| Example 31 | Methoxy | Ethyl | 194.5–195.5 | 12.60 (br.s, 1H), 9.15 (s, 1H), 8.89 (s, 2H), 7.45 (d, J = 8.6, 1H), 7.40–6.75 (m, 6H), 5.71 (dd, J = 5.5, 9.0, 1H), 5.20 (s, 2H), 3.72 (s, 3H), 3.20–1.90 (m, 6H), 0.83 (t, J = 7.0, 3H) |

TABLE 4-continued

| Example | R | R$^1$ | melting point (° C.) | $^1$HNMR (DMSO-d$_6$) (δ) |
|---|---|---|---|---|
| Example 32 | Methoxy | Propyl | 219.5–220.5 | 9.16 (s, 1H), 8.89 (s, 2H), 7.46 (d, J = 8.6, 1H), 7.40–6.75 (m, 6H), 5.80 (dd, J = 5.5, 9.0, 1H), 5.20 (s, 2H), 3.72 (s, 3H), 3.20–1.80 (m, 6H), 1.40–0.90 (m, 2H), 0.85 (t, J = 7.0, 3H) |
| Example 33 | Ethoxy | Methyl | 213.5–215.5 | 12.60 (br.s, 1H), 9.16 (s, 1H), 8.88 (s, 2H), 7.50–6.60 (m, 7H), 6.05 (q, J = 6.6, 1H), 5.19 (s, 2H), 3.96 (q, J = 7.0, 2H), 3.00–2.60 (m, 4H), 1.86 (d, J = 6.6, 3H), 12.9 (t, J = 7.0, 3H) |
| Example 34 | Ethoxy | Ethyl | 192.5–195.5 | 12.65 (br.s, 1H), 9.16 (s, 1H), 8.90 (s, 2H), 7.55–6.70 (m, 7H), 5.72 (dd, J = 5.5, 9.2, 1H), 5.21 (s, 2H), 3.98 (q, J = 6.9, 2H), 3.50–1.90 (m, 6H), 1.30 (d, J = 6.9, 3H), 0.83 (t, J = 7.0, 3H) |
| Example 35 | Ethoxy | Propyl | 216.5–217.5 | 12.68 (br.s, 1H), 9.17 (s, 1H), 8.90 (s, 2H), 7.46 (d, J = 8.6, 1H), 7.40–6.70 (m, 6H), 5.80 (dd, J = 5.5, 8.8, 1H), 5.21 (s, 2H), 3.98 (q, J = 6.9, 2H), 3.20–1.80 (m, 6H), 1.30 (d, J = 6.9, 3H), 0.84 (t, J = 6.2, 3H) |
| Example 36 | Ethoxy | Isopropyl | 183–186 | 12.65 (br.s, 1H), 9.18 (s, 1H), 8.92 (s, 2H), 7.67 (d, J = 8.1, 1H), 7.40–6.75 (m, 6H), 5.32 (d, J = 10.0, 1H), 5.24 (s, 2H), 4.00 (q, J = 6.9, 2H), 3.30–2.40 (m, 5H), 1.31 (t, J = 6.9, 3H), 0.81 (d, J = 6.6, 3H), 0.76 (d, J = 6.6, 3H) |
| Example 37 | Ethoxy | Butyl | 216–217 | 12.67 (br.s, 1H), 9.17 (s, 1H), 8.90 (s, 2H), 7.47 (d, J = 8.6, 1H), 7.40–6.75 (m, 6H), 5.79 (dd, J = 5.3, 7.7, 1H), 5.21 (s, 2H), 3.98 (q, J = 6.9, 2H), 3.20–1.80 (m, 6H), 1.30 (t, J = 6.9, 3H), 1.50–1.00 (m, 4H), 0.81 (t, J = 6.1, 3H) |
| Example 38 | 2,2,2-Trifluoroethoxy | Ethyl | 198–201 | 12.65 (br.s, 1H), 9.16 (s, 1H), 8.90 (s, 2H), 7.44 (d, J = 8.6, 1H), 7.28 (d, J = 7.5, 1H), 5.76 (dd, J = 5.1, 8.6, 1H), 5.21 (s, 2H), 4.80 (d, J = 8.9, 1H), 4.65 (d, J = 8.9, 1H), 3.20–1.90 (m, 6H), 0.83 (t, J = 7.0, 3H) |

Example 39

A. Synthesis of 2-bromo-3'-ethoxyacetophenone

While a mixture of 3'-ethoxyacetophenone (37 g, 0.225 mol), aluminum chloride (0.27 g, 2 m mol) and ether (100 ml) was stirred under cooling with ice, bromine (11.5 ml, 0.225 m mol) was added dropwise thereto over a period of 15 minutes. After this mixture was further stirred for 10 minutes, ice water (500 ml) was added thereto and this mixture was extracted with ether (2×100 ml). After the extract was washed with water and dried, the solvent was distilled off under reduced pressure. The resulting residue was distilled under reduced pressure (150–155° C./5 mmHg) to obtain the desired compound (45.7 g). Although this product contained a small amount of dibromo-substituted compounds, it was directly used in the following step.

$^1$HNMR (CDCl$_3$): δ 7.00–7.70 (m, 4H), 4.43 (s, 2H), 4.09 (q, J=7.0, 2H), 1.43 (t, J=7.0, 3H).

B. Synthesis of 2-acetoxy-3'-ethoxyacetophenone

A mixture of the compound (42.8 g, 0.176 mol) obtained in the above step A, potassium acetate (50 g, 0.51 mol) and ethanol (250 ml) was heated with stirring for 1.5 hours. Thereafter, the solvent was distilled off under reduced pressure. After chloroform (200 ml) and water (200 ml) were added to the residue, the reaction mixture was allowed to separate. The aqueous layer was extracted with chloroform (150 ml). After the combined chloroform layer was washed with water and dried, the solvent was distilled off under reduced pressure. The resulting oily residue was subjected to chromatography on silica gel (500 g) using ethyl acetate-hexane (1:5). Thus, the desired compound (13.4 g, 34%) was obtained as colorless crystals (by crystallization from hexane).

Melting point: 45.5–46.5° C.; $^1$HNMR (CDCl$_3$): δ 7.55–7.05 (m, 4H), 5.31 (s, 2H), 4.08 (q, J=7.0, 2H), 2.22 (s, 3H), 1.43 (t, J=7.0, 3H).

C. Synthesis of 2-hydroxy-3'-ethoxyacetophenone

A suspension composed of the compound (10.0 g, 45 m mol) obtained in the above step B, barium carbonate (17.8 g, 90 m mol) and water (200 ml) was heated for 18 hours. After the suspension was cooled to room temperature, the supernatant was extracted with chloroform (2×100 ml). After the extract was washed with water and dried, the solvent was distilled off under reduced pressure. The resulting residue was subjected to chromatography on silica gel (100 g) using ethyl acetate-hexane (1:2). Thus, the desired compound (2.8 g, 34%) was obtained as colorless crystals.

Melting point: 69–70.5° C.; $^1$HNMR (CDCl$_3$): δ 7.55–7.05 (m, 4H), 4.85 (d, J=4.8, 2H), 4.10 (q, J=7.0, 2H), 3.45 (t, J=4.8, 1H), 1.44 (t, J=7.0, 3H).

D. Synthesis of 4,5-dihydro-1-(3-ethoxy-α-hydroxymethylbenzyl)-7-(5-pyrimidinylmethoxy)-[1H]-benz[g]indazole-3-carboxylic acid The compound obtained in the above step C and anhydrous hydrazine were treated in the same manner as in the step A of Example 30 to synthesize 3-ethoxy-α-hydroxymethylbenzyl-hydrazine. Thereafter, this compound was successively treated in the same manner as in the steps B and C of Example 30. Thus, the desired compound was obtained as a colorless solid.

Melting point: 210–211.5° C.; $^1$HNMR (DMSO-d$_6$): δ 12.65 (br. s, 1H), 9.16 (s, 1H), 8.89 (s, 2H), 7.55–6.70 (m, 7H), 5.86 (dd, J=4.6, 8.4, 1H), 5.20 (s, 2H), 4.99 (t, J=5.0, 1H), 4.50–4.20 (m, 1H), 4.10–3.80 (m, 1H), 3.98 (q, J=7.0, 2H), 2.60–3.20 (m, 4H), 1.30 (t, J=7.0, 3H). Elemental analysis (as C$_{27}$H$_{26}$N$_4$O$_5$·1/4H$_2$O); Calculated value (%): C 66.04, H 5.49, N 11.41. Observation value (%): C 65.89, H 5.27, N 11.37.

Example 40

A. Synthesis of 3'-ethoxy-2-methoxyacetophenone

Boron trifluoride-diethyl ether complex (3 drops) and an ether solution of diazomethane were added to a solution of 2-hydroxy-3'-ethoxyacetophenone (1.6 g, 8.9 m mol) in ether (60 ml). The ether solution of diazomethane was added until thin-layer reveals that the spot of 2-hydroxy-3'-ethoxyacetophenone has disappeared. After insoluble matter was filtered off, the filtrate was concentrated under reduced pressure. The resulting residue was subjected to chromatography on silica gel (40 g) using ethyl acetate-hexane (1:4). Thus, the desired compound (1.13 g, 65%) was obtained as a colorless oily material.

$^1$HNMR (CDCl$_3$): δ 7.60–7.00 (m, 4H), 4.68 (s, 2H), 4.09 (q, J=7.0, 2H), 3.50 (s, 3H), 1.43 (t, J=7.0, 3H).

B. Synthesis of 4,5-dihydro-1-(3-ethoxy-α-methoxymethyl-benzyl)-7-(5-pyrimidinylmethoxy)-[1H]-benz[g]indazole-3-carboxylic acid The compound obtained in the above step A and anhydrous hydrazine were treated in the same manner as in the step A of Example 30 to synthesize 3-ethoxy-α-methoxymethylbenzyl-hydrazine. Thereafter, this compound was successively treated in the same manner as in the steps B and C of Example 30. Thus, the desired compound was obtained as a pale-yellow solid.

Melting point: 208.5–211° C.; $^1$HNMR (DMSO-d$_6$): δ 12.68 (br. s, 1H), 9.16 (s, 1H), 8.90 (s, 2H), 7.44 (d, J=8.6, 1H), 7.40–6.75 (m, 6H), 6.00 (dd, J=4.6, 8.8, 1H), 5.21 (s, 2H), 4.36 (dd, J=8.8, 10.0, 1H), 4.15–3.75 (m, 1H), 4.00 (q, J=7.0, 2H), 3.26 (s, 3H), 3.20–2.60 (m, 4H), 1.30 (t, J=7.0, 3H). Elemental analysis (as C$_{28}$H$_{28}$N$_4$O$_5$·1/2H$_2$O); Calculated value (%): C 66.00, H 5.74, N 11.00. Observation value (%): C 65.72, H 5.52, N 10.89.

Example 41

A. Synthesis of ethoxyacetonitrile

A mixture of chloromethyl ethyl ether (12.5 g, 0.132 mol), copper cyanide (13.0 g, 0.131 mol on the assumption that it was 90% pure) and benzene (10 ml) was heated under reflux for 15 hours. After the reaction mixture was cooled, insoluble matter was filtered off and washed with benzene (20 ml). The filtrate was distilled at atmospheric pressure to obtain the desired compound (6.9 g, 61%) as a colorless liquid (105–130° C./760 mmHg).

B. Synthesis of 3'-ethoxy-2-ethoxyacetophenone

To an ether solution (30 ml) of 3-ethoxyphenylmagnesium bromide (prepared from 5.7 g of 3-ethoxyphenyl bromide and 0.7 g of magnesium), an ether solution (20 ml) of the compound (2.3 g, 27 m mol) obtained in the above step A was added dropwise thereto in an atmosphere of nitrogen. After this mixture was stirred for 30 minutes, 1 N hydrochloric acid (20 ml) was added thereto. The ether layer was washed with water (2×20 ml) and dried, the solvent was distilled off under reduced pressure. The resulting residue was subjected to chromatography on silica gel (60 g) using ethyl acetatehexane (1:5). The resulting oily material (3.3 g) was distilled under reduced pressure to obtain the desired compound (2.4 g, 42%) as an oily material (150–155° C./5 mmHg).

$^1$HNMR (CDCl$_3$): δ 7.60–7.00 (m, 4H), 4.71 (s, 2H), 4.08 (q, J=7.0, 2H), 3.64 (q, J=7.0, 2H), 1.43 (t, J=7.0, 3H), 1.29 (t, J=7.0, 3H).

C. Synthesis of 4,5-dihydro-1-(3-ethoxy-α-ethoxymethyl-benzyl)-7-(5-pyrimidinylmethoxy)-[1H]-benz[g]indazole-3-carboxylic acid The compound obtained in the above step B was successively treated in the same manner as in the steps A, B and C of Example 30. Thus, the desired compound was obtained as a pale-yellow solid.

Melting point: 209.5–21 1° C.; $^1$HNMR (DMSO-d$_6$): δ 12.65 (br. s, 1H), 9.16 (s, 1H), 8.90 (s, 2H), 7.46 (d, J=8.6, 1H), 7.40–6.75 (m, 6H), 5.97 (dd, J=4.8, 8.6, 1H), 5.20 (s, 2H), 4.38 (dd, J=8.6, 10.0, 1H), 4.15–3.80 (m, 1H), 3.99 (q, J=7.0, 2H), 3.47 (q, J=7.0, 2H), 3.20–2.60 (m, 4H), 1.30 (t, J=7.0, 3H), 1.02 (t, J=7.0). Elemental analysis (as C$_{29}$H$_{30}$N$_4$O$_5$·1/5H$_2$O); Calculated value (%): C 67.22, H 5.91, N 10.81. Observation value (%): C 67.18, H 5.82, N 10.81.

Example 42

A. Synthesis of 3'-ethoxy-2-phenoxyacetophenone

A mixture of 2-bromo-3'-ethoxyacetophenone (2.4 g, 10 m mol), phenol (1.0 g, 10.6 m mol), potassium carbonate (2.0 g, 14.5 m mol) and acetone (30 ml) was heated under reflux for 6 hours. After insoluble matter was filtered off, the solvent was distilled off under reduced pressure. The residue was dissolved in chloroform (40 ml), washed with water (2×20 ml), and dried. Thereafter, the solvent was distilled off under reduced pressure. The resulting residue was subjected to chromatography on silica gel (50 g) using chloroform. Thus, the desired compound (1.94 g, 75%) was obtained as an oily material.

$^1$HNMR (CDCl$_3$): δ 7.65–6.80 (m, 9H), 5.24 (s, 2H), 4.08 (q, J=7.0, 2H), 1.43 (t, J=7.0, 3H).

B. Synthesis of 4,5-dihydro-1-(3-ethoxy-α-phenoxymethyl-benzyl)-7-(5-pyrimidinylmethoxy)-[1H]-benz[g]indazole-3-carboxylic acid The compound obtained in the above step A was successively treated in the same manner as in the steps A, B and C of Example 30. Thus, the desired compound was obtained as a colorless solid.

Melting point: 190–192° C.; $^1$HNMR (DMSO-$d_6$): δ 12.70 (br. s, 1H), 9.16 (s, 1H), 8.90 (s, 2H), 7.60–6.70 (m, 12H), 6.30 (dd, J=4.0, 8.5, 1H), 5.21 (s, 2H), 5.30–4.85 (m, 1H), 4.52 (dd, J=4.0, 9.5, 1H), 4.00 (q, J=7.0, 2H), 7.20–2.60 (m, 4H), 1.31 (t, J=7.0, 3H). Elemental analysis (as $C_{33}H_{30}N_4O_5 \cdot 1/4H_2O$); Calculated value (%): C 69.89, H 5.42, N 9.88. Observation value (%): C 69.77, H 5.26, N 10.05.

Example 43

A. Synthesis of 3-ethoxy-α-phenylbenzyl alcohol

To an ether solution of phenylmagnesium bromide [prepared from bromobenzene (3.69 ml, 35 m mol), magnesium (0.95 g, 39 m mol) and ether (50 ml)], an ether solution (30 ml) of 3-ethoxybenzaldehyde (3.0 g, 20 m mol) was added dropwise thereto with stirring and under cooling with ice. After 30 minutes, 1 N hydrochloric acid (20 ml) was added thereto. The ether layer was separated and the aqueous layer was extracted with ether (20 ml). After the combined ether layer was washed with a saturated aqueous solution of sodium chloride (15 ml) and dried, the solvent was distilled off under reduced pressure. The resulting residue was subjected to chromatography on silica gel (100 g) using hexane, and eluted with hexane and then with hexane-ethyl acetate (5:1). The resulting yellow oily material containing the desired compound was distilled to obtain the desired compound (2.9 g, 60%) as a colorless oily material (150–153° C./1–2 mmHg).

B. Synthesis of 3-ethoxy-α-phenylbenzyl bromide

Pyridine (2 ml, 24.7 m mol) and phosphorus tribromide (4.3 ml, 23.6 m mol) were added dropwise to a solution in benzene (30 ml) of the compound (2.68 g, 11.7 m mol) obtained in the above step A, and this mixture was stirred for 18 hours. After the reaction mixture was poured into ice water (50 ml), the benzene layer was separated and the aqueous layer was extracted with benzene (30 ml). After the combined benzene layer was washed with water and dried, the solvent was distilled off under reduced pressure. The resulting oily residue was subjected to chromatography on silica gel (40 g) using hexane-ethyl acetate (10:1). Thus, the desired compound (2.0 g, 58%) was obtained as an oily material.

$^1$HNMR (CDCl$_3$): δ 7.55–7.10 (m, 6H), 7.10–6.90 (m, 2H), 6.70–6.90 (m, 1H), 6.23 (s, 1H), 4.01 (q, J=7.0, 2H), 1.39 (t, J=7.0, 3H).

C. Synthesis of 3-ethoxy-α-phenylbenzylhydrazine

While a solution of hydrazine monohydrate (5 ml, 0.1 mol) in ethanol (10 ml) was heated under reflux, a solution in ethanol (5 ml) of the compound (0.9 g, 3 m mol) obtained in the above step B was added dropwise thereto over a period of 10 minutes. After this mixture was further refluxed for 3 hours, the solvent was distilled off under reduced pressure. The resulting oily residue was subjected to chromatography on silica gel (40 g) using chloroform-methanol (100:1), and eluted with chloroform-methanol (20:1). Thus, the desired compound (490 mg, 67%) was obtained as a pale-yellow oily material.

$^1$HNMR (CDCl$_3$): δ 7.50–7.10 (m, 6H), 7.05–6.85 (m, 2H), 6.85–6.70 (m, 1H), 4.80 (s, 1H), 4.00 (q, J=7.0, 2H), 3.35 (br. s, 3H), 1.38 (t, J=7.0, 3H).

D. Synthesis of 4,5-dihydro-1-(3-ethoxy-α-phenylbenzyl)-7-(5-pyrimidinylmethoxy)-[1H]-benz[g]indazole-3-carboxylic acid The compound obtained in the above step C was successively treated in the same manner as in the steps B and C of Example 2. Thus, the desired compound was obtained as a colorless solid.

Melting point: 275–276° C. (decomposition point); $^1$HNMR (DMSO-$d_6$): δ 12.65 (br. s, 1H), 9.16 (s, 1H), 8.90 (s, 2H), 7.60–6.70 (m, 13H), 5.21 (s, 2H), 3.96 (q, J=7.0, 2H), 2.87 (s, 4H), 1.28 (t, J=7.0, 3H). Elemental analysis (as $C_{32}H_{28}N_4O_4 \cdot 1/5H_2O$); Calculated value (%): C 71.68, H 5.34, N 10.45. Observation value (%): C 71.64, H 5.23, N 10.43.

Examples 44 to 50

Corresponding starting compounds were treated in the same manner as in Example 43 to obtain the compounds shown in Table 5.

TABLE 5

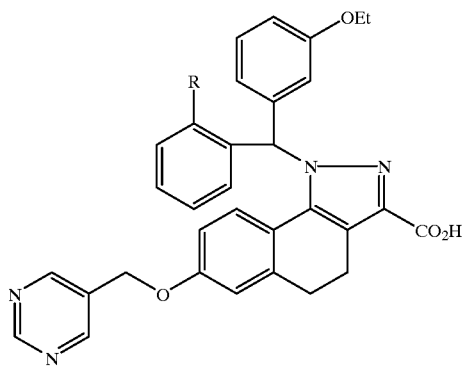

| Example | R | melting point (° C.) | $^1$HNMR (CDCl$_3$) (δ) |
|---|---|---|---|
| Example 44 | Methyl | 245.5–248 | 9.22 (s, 1H), 8.81 (s, 2H), 7.40–6.55 (m, 12H), 5.09 (s, 2H), 3.97 (q, J = 7.0, 2H), 3.20–2.75 (m, 4H), 2.07 (s, 3H), 1.37 (t, J = 7.0, 3H) |

TABLE 5-continued

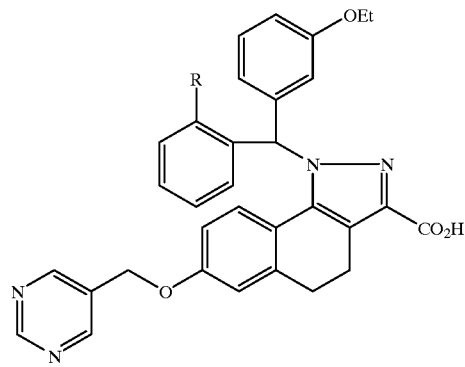

| Example | R | melting point (° C.) | $^1$HNMR (CDCl$_3$) (δ) |
|---|---|---|---|
| Example 45 | Methyl | 237–239 | 9.22 (s, 1H), 8.82 (s, 2H), 7.40–6.55 (m, 12H), 5.09 (s, 2H), 3.97 (q, J = 7.0, 2H), 3.20–2.70 (m, 4H), 2.43 (q, J = 7.4, 2H), 1.37 (t, J = 7.0, 3H), 0.98 (t, J = 7.4, 3H) |
| Example 46 | Ethyl | 212–214 | 9.22 (s, 1H), 8.83 (s, 2H), 7.50–6.60 (m, 12H), 5.09 (s, 2H), 3.96 (q, J = 7.0, 2H), 3.70 (s, 3H), 3.20–2.70 (m, 4H), 1.36 (t, J = 7.0, 3H) |
| Example 47 | Ethoxy | 184–189 | 9.22 (s, 1H), 8.83 (s, 2H), 7.55–6.60 (m, 12H), 5.09 (s, 2H), 3.97 (q, J = 7.0, 2H), 3.89 (q, J = 7.0, 2H), 3.25–2.70 (m, 4H), 1.36 (t, J = 7.0, 3H), 1.03 (t, J = 7.0, 3H) |
| Example 48 | Propoxy | 162.5–164 | 9.21 (s, 1H), 8.83 (s, 2H), 7.60–6.60 (m, 12H), 5.09 (s, 2H), 3.97 (q, J = 7.0, 2H), 3.81 (t, J = 6.3, 2H), 3.30–2.75 (m, 4H), 1.70–1.15 (m, 2H), 1.37 (t, J = 7.0, 3H), 0.68 (t, J = 7.3, 3H) |
| Example 49 | Isopropoxy | 108.5–142.5 | 9.21 (s, 1H), 8.83 (s, 2H), 7.50–6.60 (m, 12H), 5.10 (s, 2H), 4.70–4.25 (m, 1H), 3.98 (q, J = 7.0, 2H), 3.20–2.70 (m, 4H), 1.37 (t, J = 7.0, 3H), 1.02 (d, J = 6.2, 3H), 0.94 (d, J = 5.9, 3H) |
| Example 50 | Butoxy | 145–152 | 9.22 (s, 1H), 8.82 (s, 2H), 7.55–6.55 (m, 12H), 5.09 (s, 2H), 3.97 (q, J = 7.0, 2H), 3.85 (t, J = 6.0, 2H), 3.30–2.70 (m, 4H), 1.37 (t, J = 7.0, 3H), 1.60–0.80 (m, 4H), 0.69 (d, J = 6.3, 3H) |

Example 51

A. Synthesis of 3-ethoxy-α-(2-chlorophenyl)benzyl alcohol

To an ether solution of 3-ethoxyphenylmagnesium bromide [prepared from 3-ethoxybromobenzene (6 g, 30 m mol), magnesium (0.8 g, 33 m mol) and ether (30 ml)], an ether solution (30 ml) of 2-chlorobenzaldehyde (2.8 g, 20 m mol) was added dropwise with stirring and under cooling with ice. After 30 minutes, 1 N hydrochloric acid (50 ml) was added thereto. The ether layer was separated and the aqueous layer was extracted with ether (20 ml). After the combined ether layer was washed with a saturated aqueous solution of sodium chloride (15 ml) and dried, the solvent was distilled off under reduced pressure. The resulting residue was subjected to chromatography on silica gel (60 g) using hexane-ethyl acetate (5:1). The resulting fraction containing the desired compound was distilled to obtain the desired compound (3.4 g, 64%) as a colorless oily material (178–179° C./1 mmHg).

B. Synthesis of 4,5-dihydro-1-[3-ethoxy-α-(2-chlorophenyl)-benzyl]-7-(5-pyrimidinylmethoxy)-[1H]-benz[g]indazole-3-carboxylic acid The compound obtained in the above step A was successively treated in the same manner as in the steps B, C and D of Example 43. Thus, the desired compound was obtained as a colorless solid.

Melting point: 233.5–235° C.; $^1$HNMR (DMSO-d$_6$): δ 12.65 (br. s, 1H), 9.16 (s, 1H), 8.90 (s, 2H), 7.60–6.65 (m, 12H), 5.21 (s, 2H), 3.97 (q, J=7.0, 2H), 2.87 (s, 4H), 1.29 (t, J=7.0, 3H). Elemental analysis (as C$_{32}$H$_{27}$ClN$_4$O$_4$); Calculated value (%): C 67.78, H 4.80, N 9.88. Observation value (%): C 68.00, H 4.75, N 9.95.

Examples 52 to 74

Corresponding starting compounds were treated in the same manner as in Example 51 to obtain the compounds shown in Tables 6 and 7.

TABLE 6

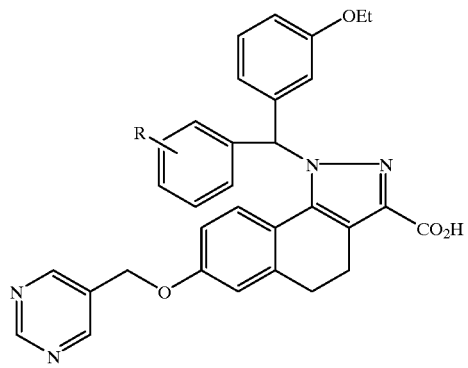

| Example | R | melting point (° C.) | ¹HNMR (DMSO-d₆) (δ) |
|---|---|---|---|
| Example 52 | 2-Bromo | 224–225 | 12.65 (br.s, 1H), 9.16 (s, 1H), 8.90 (s, 2H), 7.75–6.65 (m, 12H), 5.20 (s, 2H), 3.97 (q, J = 7.0, 2H), 2.88 (s, 4H), 1.28 (t, J = 7.0, 3H) |
| Example 53 | 2-Propyl | 211–215 | 12.65 (br.s, 1H), 9.16 (s, 1H), 8.89 (s, 2H), 7.45–6.70 (m, 12H), 5.21 (s, 2H), 3.98 (q, J = 7.0, 2H), 3.20–2.60 (m, 4H), 2.60–2.25 (m, 2H), 1.50–0.80 (m, 2H), 1.29 (t, J = 7.0, 3H), 0.62 (t, J = 7.0, 3H) |
| Example 54 | 2-Isopropyl | 215.5–218.5 | 12.65 (br.s, 1H), 9.16 (s, 1H), 8.89 (s, 2H), 7.45–6.65 (m, 12H), 5.20 (s, 2H), 3.97 (q, J = 7.0, 2H), 2.87 (m, 4H), 3.20–2.70 (m, 1H), 1.28 (t, J = 7.0, 3H), 0.93 (d, J = 6.6, 6H) |
| Example 55 | 2-Phenyl | 160.5–163 | 12.65 (br.s, 1H), 9.18 (s, 1H), 8.89 (s, 2H), 7.50–6.55 (m, 17H), 5.19 (s, 2H), 3.96 (q, J = 7.0, 2H), 3.20–2.60 (m, 4H), 1.28 (t, J = 7.0, 3H) |
| Example 56 | 2-Benzyloxy | 203.5–205.5 | 12.65 (br.s, 1H), 9.16 (s, 1H), 8.90 (s, 2H), 7.55–6.60 (m, 17H), 5.20 (s, 2H), 5.05 (s, 2H), 3.94 (q, J = 7.0, 2H), 3.20–2.60 (m, 4H), 1.27 (t, J = 7.0, 3H) |
| Example 57 | 3-Ethoxy | 243–244 | 9.16 (s, 1H), 8.89 (s, 2H), 7.60–6.65 (m, 12H), 5.21 (s, 2H), 3.96 (q, J = 7.0, 4H), 2.89 (s, 4H), 1.28 (t, J = 7.0, 6H) |
| Example 58 | 3-(2,2,2-Trifluoroethoxy) | 261.5–262.5 | 12.65 (br.s, 1H), 9.16 (s, 1H), 8.90 (s, 2H), 7.60–6.65 (m, 12H), 5.22 (s, 2H), 4.78 (d, J = 8.8, 1H), 4.62 (d, J = 8.8, 1H), 3.96 (q, J = 7.0, 2H), 2.87 (s, 4H), 1.28 (t, J = 7.0, 1H) |
| Example 59 | 2-Trifluoromethyl | 226–227 | 12.70 (br.s, 1H), 9.17 (s, 1H), 8.90 (s, 2H), 7.85–6.50 (m, 12H), 5.20 (s, 2H), 3.97 (q, J = 7.0, 2H), 3.20–2.60 (m, 4H), 1.28 (t, J = 7.0, 3H) |
| Example 60 | 4-Methyl | 240–242 | 9.22 (s, 1H), 8.82 (s, 2H), 7.40–6.65 (m, 12H), 5.09 (s, 2H), 3.97 (q, J = 7.0, 2H), 3.20–2.70 (m, 4H), 2.35 (s, 3H), 1.37 (t, J = 7.0, 3H)* |
| Example 61 | 2,3-Dimethoxy | 212–214.5 | 12.65 (br.s, 1H), 9.16 (s, 1H), 8.90 (s, 2H), 7.55–6.45 (m, 11H), 5.21 (s, 2H), 3.97 (q, J = 7.0, 2H), 3.81 (s, 3H), 3.33 (s, 3H), 2.87 (s, 4H), 1.28 (t, J = 7.0, 3H) |
| Example 62 | 2,5-Dimethoxy | 198–200 | 12.65 (br.s, 1H), 9.17 (s, 1H), 8.90 (s, 2H), 7.55–6.55 (m, 11H), 5.21 (s, 2H), 3.95 (q, J = 7.0, 2H), 3.66 (s, 3H), 3.63 (s, 3H), 2.86 (s, 4H), 1.28 (t, J = 7.0, 3H) |
| Example 63 | 2,6-Dimethoxy | 198.5–200 | 12.50 (br.s, 1H), 9.16 (s, 1H), 8.88 (s, 2H), 7.55–6.40 (m, 11H), 5.17 (s, 2H), 3.91 (q, J = 7.0, 2H), 3.54 (s, 6H), 3.10–270 (m, 4H), 1.28 (t, J = 7.0, 3H) |
| Example 64 | 2,3-Methylenedioxy | 243–244.5 | 12.65 (br.s, 1H), 9.16 (s, 1H), 8.90 (s, 2H), 7.55–6.50 (m, 11H), 5.99 (s, 2H), 5.21 (s, 2H), 3.96 (q, J = 7.0, 2H), 2.87 (s, 4H), 1.28 (t, J = 7.0, 3H) |
| Example 65 | 3,4,5-Trimethoxy | 195.5–198 | 12.60 (br.s, 1H), 9.16 (s, 1H), 8.90 (s, 2H), 7.52 (d, J = 8.6, 1H), 7.40–6.65 (m, 9H), 5.22 (s, 2H), 3.96 (q, J = 7.0, 2H), 3.67 (s, 9H), 2.87 (s, 4H), 1.28 (t, J = 7.0, 3H) |

*¹HNMR (CDCl₃)

TABLE 7

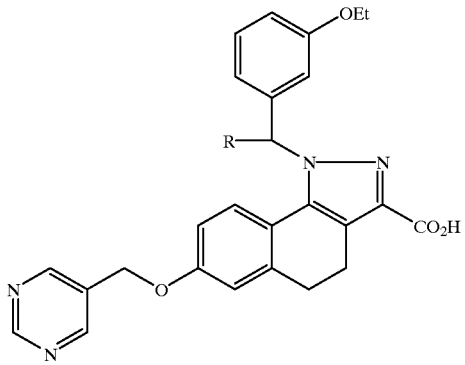

| Example | R | melting point (° C.) | ¹HNMR (DMSO-d₆) (δ) |
|---|---|---|---|
| Example 66 | 1-Naphthyl | 262.5–263.5 | 12.60 (br.s, 1H), 9.15 (s, 1H), 8.86 (s, 2H), 6.70–8.05 (m, 15H), 5.17 (s, 2H), 3.96 (q, J = 7.0, 2H), 2.90 (s, 4H), 1.27 (t, J = 7.0, 3H) |
| Example 67 | 2-Naphthyl | 222.5–226.5 | 12.65 (br.s, 1H), 9.16 (s, 1H), 8.89 (s, 2H), 6.70–8.00 (m, 15H), 5.20 (s, 2H), 3.96 (q, J = 7.0, 2H), 2.89 (s, 4H), 1.27 (t, J = 7.0, 3H) |
| Example 68 | Cyclopropyl | 185–186.5 | 12.55 (br.s, 1H), 9.18 (s, 1H), 8.93 (s, 2H), 7.66 (d, J = 8.4, 1H), 6.65–7.30 (m, 7H), 6.05–6.55 (m, 2H), 5.23 (s, 2H), 4.45–4.75 (m, 2H), 3.99 (q, J = 7.0, 2H), 2.83 (s, 4H), 2.60–3.00 (m, 1H), 1.31 (t, J = 7.0, 3H) |
| Example 69 | Cyclohexyl | 238–240.5 | 12.65 (br.s, 1H), 9.17 (s, 1H), 8.91 (s, 2H), 7.65 (d, J = 8.1, 1H), 6.75–7.40 (m, 6H), 5.35 (d, J = 10.1, 1H), 5.23 (s, 2H), 4.00 (q, J = 7.0, 2H), 2.40–3.30 (m, 5H), 1.32 (t, J = 7.0, 3H), 0.70–1.80 (m, 10H) |
| Example 70 | 2-Pyridyl | 219.5–222 (dec.) | 9.17 (s, 1H), 8.91 (s, 2H), 8.55–8.70 (m, 1H), 7.80–8.05 (m, 1H), 6.70–7.60 (m, 10H), 5.22 (s, 2H), 3.97 (q, J = 7.0, 2H), 2.88 (s, 4H), 1.29 (t, J = 7.0, 3H) |
| Example 71 | 3-Pyridyl | 285–286.5 (dec.) | 9.16 (s, 1H), 8.90 (s, 2H), 8.40–8.60 (m, 2H), 6.60–6.75 (m, 10H), 5.22 (s, 2H), 3.96 (q, J = 7.0, 2H), 2.70–3.10 (m, 4H), 1.28 (t, J = 7.0, 3H) |
| Example 72 | 4-Pyridyl | 274.5–276.5 (dec.) | 12.70 (br.s, 1H), 9.16 (s, 1H), 8.90 (s, 2H), 8.55 (d, J = 5.7, 2H), 6.75–7.60 (m, 10H), 5.22 (s, 2H), 3.97 (q, J = 7.0, 2H), 2.88 (s, 4H), 1.29 (t, J = 7.0, 3H) |
| Example 73 | 2-Pyrimidinyl | 182–193 (dec.) | 9.16 (s, 1H), 8.89 (s, 2H), 8.78 (d, J = 4.8, 2H), 6.75–7.55 (m, 9H), 5.20 (s, 2H), 3.97 (q, J = 7.0, 2H), 2.86 (s, 4H), 1.29 (t, J = 7.0, 3H) |
| Example 74 | 3-Pyridazinyl | 231–234 (dec.) | 9.23 (dd, J = 1.5, 3.1, 1H), 9.16 (s, 1H), 8.90 (s, 2H), 6.70–7.90 (m, 9H), 5.22 (s, 2H), 3.97 (q, J = 7.0, 2H), 2.88 (s, 4H), 1.28 (t, J = 7.0, 3H) |

Example 75

A. Synthesis of α-(3-methoxypyridin-2-yl)-3-ethoxybenzyl alcohol

To a solution of 2-bromomesitylene (9.16 ml, 60 m mol) in tetrahydrofuran (250 ml), a 1.64 M pentane solution of tert-butyl lithium (73 ml, 120 m mol) was added dropwise at −50° C. or below. After this mixture was stirred for 30 minutes, 3-methoxypyridine (5.0 g, 46 m mol) was added dropwise thereto at −50° C. or below and the resulting mixture was stirred at −20° C. for 2 hours. After the reaction mixture was cooled again to −50° C. or below, 3-ethoxybenzaldehyde (10.3 g, 69 m mol) was added dropwise thereto and the stirring was continued for another 30 minutes. After the addition of a saturated aqueous solution of sodium chloride (10 ml), the reaction mixture was returned to room temperature. After a saturated aqueous solution of sodium chloride (200 ml) was further added thereto, the organic layer was separated. The aqueous layer was extracted with ethyl acetate (200 ml), and the extract was combined with the previous organic layer. After the combined organic layer was washed with a saturated aqueous solution of sodium chloride (50 ml) and dried over magnesium sulfate, the solvent was distilled off under reduced pressure. The resulting solid was washed with hexane and then recrystallized from methanol (300 ml) to obtain the desired compound (7.0 g, 59%) as colorless crystals.

Melting point: 104.5–106° C.; ¹HNMR (CDCl₃): δ 8.17 (dd, J=4.0, 1.9, 1H), 7.30–6.60 (m, 6H), 5.92 (d, J=7.3, 1H), 5.35 (d, J=7.3, 1H), 3.99 (q, J=7.0, 2H), 3.76 (s, 3H), 1.37 (t, J=7.0, 3H).

B. Synthesis of 4,5-dihydro-1-[α-(3-methoxypyridin-2-yl)-3-ethoxybenzyl]-7-(5-pyrimidinylmethoxy)- [1H]-benz[g]indazole-3-carboxylic acid The compound obtained in the above step A was successively treated in the same manner as in the steps B, C and D of Example 43. Thus, the desired compound was obtained as a colorless solid.

Melting point: 222.5–225° C.; ¹HNMR (DMSO-d₆): δ 9.17 (s, 1H), 8.90 (s, 2H), 8.06 (dd, J=4.2, 1.4, 1H), 6.60–7.60 (m, 9H), 5.20 (s, 2H), 3.94 (q, J=7.0, 2H), 3.68 (s, 3H), 2.85 (s, 4H), 1.28 (t, J=7.0, 3H). Elemental analysis (as C₃₂H₂₉N₅O₅. 1/2H₂O); Calculated value (%): C 67.11, H 5.28, N 12.23. Observation value (%): C 67.37, H 5.09, N 12.16.

Example 76

A. Synthesis of 6-benzyloxy-1-oxo-1,2,3,4-tetrahydronaphtho-2-glyoxylic acid methyl ester 6-Benzyloxy-1-oxo-1,2,3,4-tetrahydronaphthalene was treated in the same manner as in the step C of Example 1 to obtain the desired compound.

Melting point: 80–81° C.; $^1$HNMR (CDCl$_3$): δ 7.98 (d, J=8.6, 1H), 7.50–7.25 (m, 5H), 6.93 (dd, J=2.4, 8.6, 1H), 6.79 (d, J=2.4, 1H), 5.12 (s, 2H), 3.90 (s, 3H), 3.10–2.70 (m, 4H).

B. Synthesis of 1-benzyl-7-benzyloxy-4,5-dihydro-[1H]-benz[g]indazole-3-carboxylic acid methyl ester The compound obtained in the above step A was treated in the same manner as in the step D of Example 1 to obtain the desired compound.

Melting point: 168–169° C.; $^1$HNMR (CDCl$_3$): δ 7.50–7.00, (m, 11H), 6.94 (d, J=2.4, 1H), 6.71 (dd, J=2.4, 8.6, 1H), 5.69 (s, 2H), 5.03 (s, 2H), 3.95 (s, 3H), 3.20–2.75 (m, 4H).

C. Synthesis of 1-benzyl-4,5-dihydro-7-hydroxy-[1H]-benz[g]indazole-3-carboxylic acid methyl ester Under an atmosphere of hydrogen, a mixture of the compound (550 mg, 1.17 m mol) obtained in the above step B, 5% palladium-carbon (150 mg) and N,N-dimethylformamide (15 ml) was stirred for 6 hours. After the catalyst was filtered off, the solvent was distilled off under reduced pressure. The resulting residue was subjected to chromatography on silica gel (30 g) using chloroformmethanol (100:1). Thus, the desired compound (390 mg, 100%) was obtained as a colorless solid.

$^1$HNMR (DMSO-d6): δ 9.61 (s, 1H), 7.45–6.95 (m, 6H), 6.75 (d, J=2.4, 1H), 6.57 (dd, J=2.4, 8.6, 1H), 5.70 (s, 1H), 3.81 (s, 3H), 3.00–2.60 (m, 4H).

D. Synthesis of 1-benzyl-4,5-dihydro-7-(5-pyrimidinyl-methoxy)-[1H]-benz[g]indazole-3-carboxylic acid methyl ester To a suspension of sodium hydride (1.2 m mol) in N,N-dimethylformamide (5 ml), the compound (370 mg, 1.1 m mol) obtained in the above step C was added with stirring and under cooling with ice. After 20 minutes, a solution of 5-chloromethylpyrimidine (167 mg, 1.3 m mol) in N,N-dimethylformamide (3 ml) was added dropwise thereto. After the stirring was continued for another 3 hours, the solvent was distilled off under reduced pressure. The resulting residue was dissolved in chloroform (15 ml), washed with water, and dried (over magnesium sulfate). After solvent was distilled off under reduced pressure, the resulting residue was subjected to chromatography on silica gel (20 g) using ether, and eluted with chloroform. Thus, the desired compound (350 mg, 75%) was obtained as colorless crystals.

Melting point: 202–203° C.; $^1$HNMR (CDCl$_3$): δ 9.21 (s, 1H), 8.81 (s, 2H), 7.45–6.90 (m, 7H), 6.72 (dd, J=2.6, 8.4, 1H), 5.71 (s, 2H), 5.06 (s, 2H), 3.95 (s, 3H), 3.20–2.80 (m, 4H).

Example 77

Synthesis of 4,5-dihydro-1-(3-ethoxy-α-ethylbenzyl)-7-(5-pyrimidinylmethoxy)-[1H]-benz[g]indazole-3-carboxylic acid sodium salt The 4,5-dihydro-1-(3-ethoxy-α-ethylbenzyl)-7-(5-pyrimidinylmethoxy)-[1H]-benz[g]indazole-3-carboxylic acid (600 mg, 1.23 m mol) obtained in Example 34 was suspended in water (20 ml) and dissolved therein by the addition of 1 N sodium hydroxide (2 ml). This solution was subjected to column chromatography using a CHP 20P resin (20 ml; manufactured by Mitsubishi Chemical Co., Ltd.), and eluted successively with water and 50% ethanol-water. After the 50% ethanol-water fraction was concentrated under reduced pressure, the residue was dissolved in water (30 ml) and this solution was concentrated again under reduced pressure. Thereafter, the residue was dissolved in water (15 ml) and freeze-dried to obtain the desired compound (500 mg, 80%) as a colorless powder.

Melting point: 260.5–263° C.; $^1$HNMR (DMSO-d$_6$): δ 9.16 (s, 1H), 8.89 (s, 2H), 6.65–7.45 (m, 9H), 5.58 (dd, J=5.1, 8.6, 1H), 5.19 (s, 2H), 3.96 (q, J=7.0, 2H), 1.90–3.00 (m, 6H), 1.28 (t, J=7.0, 3H), 0.81 (t, J=7.0, 3H). Elemental analysis (as $C_{28}H_{27}N_4O_4Na \cdot 2/3H_2O$); Calculated value (%): C 64.86, H 5.51, N 10.80. Observation value (%): C 64.67, H 5.21, N 10.59.

| Preparation Example A: Tablets | |
|---|---|
| | mg/tablet |
| Active ingredient | 100 |
| Starch | 20 |
| Lactose | 105.5 |
| Carboxymethylcellulose calcium | 20 |
| Talc | 3 |
| Magnesium stearate | 1.5 |
| | 250 mg |

After the active ingredient is ground to a particle size of 70 microns or less, starch, lactose and carboxymethylcellulose calcium are added thereto and mixed intimately therewith. 10% starch paste is added to the aforesaid powder mixture and blended therewith by agitation to form granules. After drying, the granules were adjusted to a size of around 1,000 microns, and then blended with talc and magnesium stearate. The resulting blend is formed into tablets.

What is claimed is:

1. A 4,5-dihydro-[1H]-benz[g]indazole-3-carboxylic acid derivative represented by the following formula, or a salt thereof:

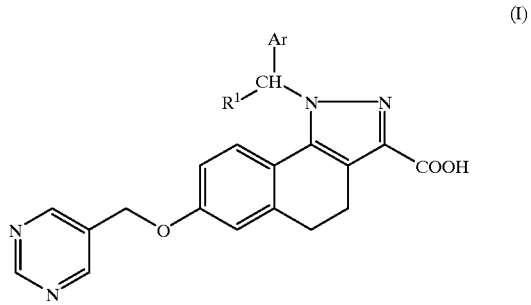

(I)

wherein Ar represents a phenyl or naphthyl group which may be substituted by 1 to 3 substituents selected from the group consisting of lower alkyl groups, lower alkoxy groups, halogen-substituted lower alkoxy groups, lower alkoxy-substituted lower alkoxy groups, carboxy-substituted lower alkoxy groups, lower alkylthio groups, lower alkylenedioxy groups, halogen atoms, a hydroxyl group, a nitro group and an amino group, and $R^1$ represents a hydrogen atom; a lower alkyl group; a hydroxy-substituted lower alkyl group; a lower alkyl-substituted lower alkyl group; a phenoxy-substituted lower alkyl group; a phenyl group which may be substituted by 1 to 3 substituents selected from the group consisting of lower alkyl groups, halogen-substituted lower alkyl groups, lower alkoxy groups, halogen-substituted lower alkoxy groups, aralkyloxy groups, lower alkylenedioxy groups, halogen atoms and a phenyl group; a naphthyl group; a cycloalkyl group; or a heterocyclic group selected from the group consisting of pyrrolyl, imidazolyl, pyrazolyl, triazolyl, tetrazolyl, oxazolyl, isoxazolyl, thiazolyl, thiadiazolyl, pyridyl, pyrazinyl, pyrimidinyl, pyridazinyl, benzothienyl, benzofuranyl, indolyl, benzothiazolyl, quinolyl, isoquinolyl, pyridinothiazolyl, pyrrolidinyl and piperidinyl and which may be substituted by 1 or 2 substituents selected from the group consisting of lower alkyl groups, lower alkoxy groups, halogen atoms and a nitro group.

2. A 4,5-dihydro-[1H]-benz[g]indazole-3-carboxylic acid lower alkyl ester derivative represented by the formula

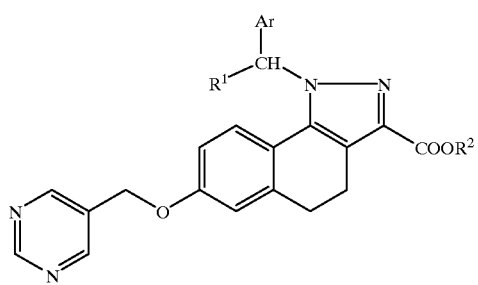

(IV)

wherein $R^2$ represents a lower alkyl group,

Ar represents a phenyl or naphthyl group which may be substituted by 1 to 3 substituents selected from the group consisting of lower alkyl groups, lower alkoxy groups, halogen-substituted lower alkoxy groups, lower alkoxy-substituted lower alkoxy groups, carboxy-substituted lower alkoxy groups, lower alkylthio groups, lower alkylenedioxy groups, halogen atoms, a hydroxyl group, a nitro group and an amino group, and $R^1$ represents a hydrogen atom; a lower alkyl group; a hydroxy-substituted lower alkyl group; a lower alkyl-substituted lower alkyl group; a phenoxy-substituted lower alkyl group; a phenyl group which may be substituted by 1 to 3 substituents selected from the group consisting of lower alkyl groups, halogen-substituted lower alkyl groups, lower alkoxy groups, halogen-substituted lower alkoxy groups, aralkyloxy groups, lower alkylenedioxy groups, halogen atoms and a phenyl group; a naphthyl group; a cycloalkyl group; or a heterocyclic group selected from the group consisting of pyrrolyl, imidazolyl, pyrazolyl, triazolyl, tetrazolyl, oxazolyl, isoxazolyl, thiazolyl, thiadiazolyl, pyridyl, pyrazinyl, pyrimidinyl, pyridazinyl, benzothienyl, benzofuranyl, indolyl, benzothiazolyl, quinolyl, isoquinolyl, pyridinothiazolyl, pyrrolidinyl and piperidinyl and which may be substituted by 1 or 2 substituents selected from the group consisting of lower alkyl groups, lower alkoxy groups, halogen atoms and a nitro group.

3. A 4,5-dihydro-[1H]-benz[g]indazole-3-carboxylic acid derivative or a salt thereof as claimed in claim 1 wherein Ar is a phenyl group substituted by one lower alkoxy group.

4. A 4,5-dihydro-[1H]-benz[g]indazole-3-carboxylic acid derivative or a salt thereof as claimed in claim 1 wherein the heterocyclic group is a five- or six-membered monocyclic aromatic heterocyclic group which contains 1 or 2 nitrogen atoms.

5. A 4,5-dihydro-[1H]-benz[g]indazole-3-carboxylic acid derivative or a salt thereof as claimed in claim 1 wherein $R^1$ is a lower alkyl group or a six-membered monocyclic aromatic heterocyclic group which contains 1 or 2 nitrogen atoms.

6. A 4,5-dihydro-[1H]-benz[g]indazole-3-carboxylic acid derivative or a salt thereof as claimed in claim 1 wherein Ar is a 3-ethoxyphenyl group and $R^1$ is an ethyl group or a 2-pyridyl group.

7. A pharmaceutical composition comprising a 4,5-dihydro-[1H]-benz[g]indazole-3-carboxylic acid derivative or a salt thereof as claimed in claim 1, and a pharmaceutically acceptable adjuvant.

8. A method for the treatment of post-PTCA restenosis in a human or other mammal which comprises administering a therapeutically effective amount of a 4,5-dihydro-[1H]-benz[g]indazole-3-carboxylic acid derivative or a salt thereof as claimed in claim 1 to the human or other mammal.

9. A compound represented by the formula

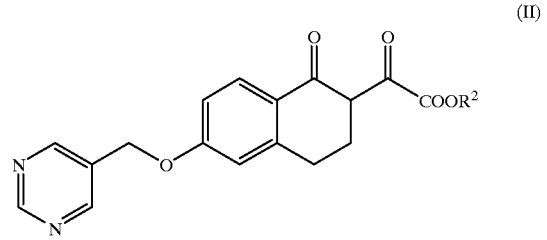

(II)

wherein $R^2$ represents a lower alkyl group.

* * * * *